United States Patent [19]

Oswald et al.

[11] Patent Number: 4,973,764
[45] Date of Patent: Nov. 27, 1990

[54] ALKYLPHENOLS AND DERIVATIVES THEREOF VIA PHENOL ALKYLATION BY CRACKED PETROLEUM DISTILLATES

[75] Inventors: Alexis A. Oswald, Annandale, N.J.; Ram N. Bhatia, Baton Rouge, La.; Edmund J. Mozeleski, Califon; Darrell W. Brownawell, Scotch Plains, both of N.J.; Thomas L. Ashcraft, Baytown, Tex.

[73] Assignee: Exxon Research and Engineering Company, Florham Park, N.J.

[21] Appl. No.: 435,237

[22] Filed: Nov. 13, 1989

Related U.S. Application Data

[63] Continuation-in-part of Ser. No. 113,619, Oct. 26, 1987, Pat. No. 4,914,246, which is a continuation-in-part of Ser. No. 922,877, Oct. 24, 1986, abandoned.

[51] Int. Cl.$^5$ ............... C07C 43/174; C07C 37/11
[52] U.S. Cl. ............... 568/649; 568/630; 568/650; 568/788; 568/790; 568/793
[58] Field of Search ............ 568/630, 649, 650, 793, 568/788, 790

[56] References Cited

U.S. PATENT DOCUMENTS

| 4,339,612 | 7/1982 | Krant et al. | 568/649 |
| 4,409,403 | 10/1983 | Vaughan | 568/649 |
| 4,914,246 | 4/1990 | Oswald et al. | 568/793 |

FOREIGN PATENT DOCUMENTS 534559 12/1956 Canada ..................... 568/649

*Primary Examiner*—Werren B. Lone
*Attorney, Agent, or Firm*—J. J. Mahon

[57] ABSTRACT

There are disclosed novel compositions of matter comprising monoalkylphenols prepared by selectively alkylating the olefin component of a thermally cracked sulfur-containing petroleum distillate derived from residua. The monoalkylphenols have certain ortho to para ratios and may be used to prepare a number of useful derivatives such as ethoxylated and propoxylated surfactants, sulfoalkylated products, sulfurized antioxidants, overbased phenates, dithiophosphate derivatives, formaldehyde reaction products and similar methylene bridged products which are useful demulsifiers.

5 Claims, 6 Drawing Sheets

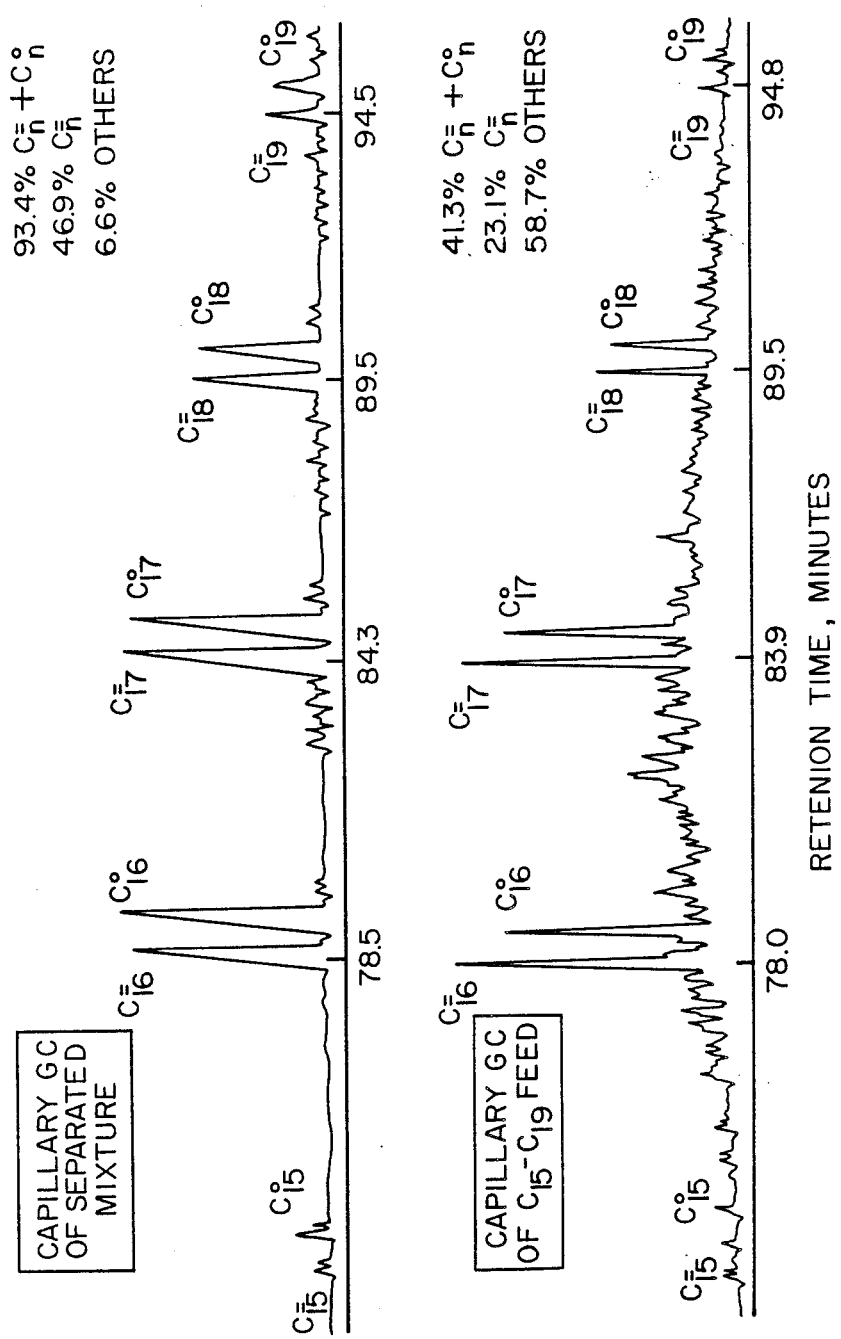

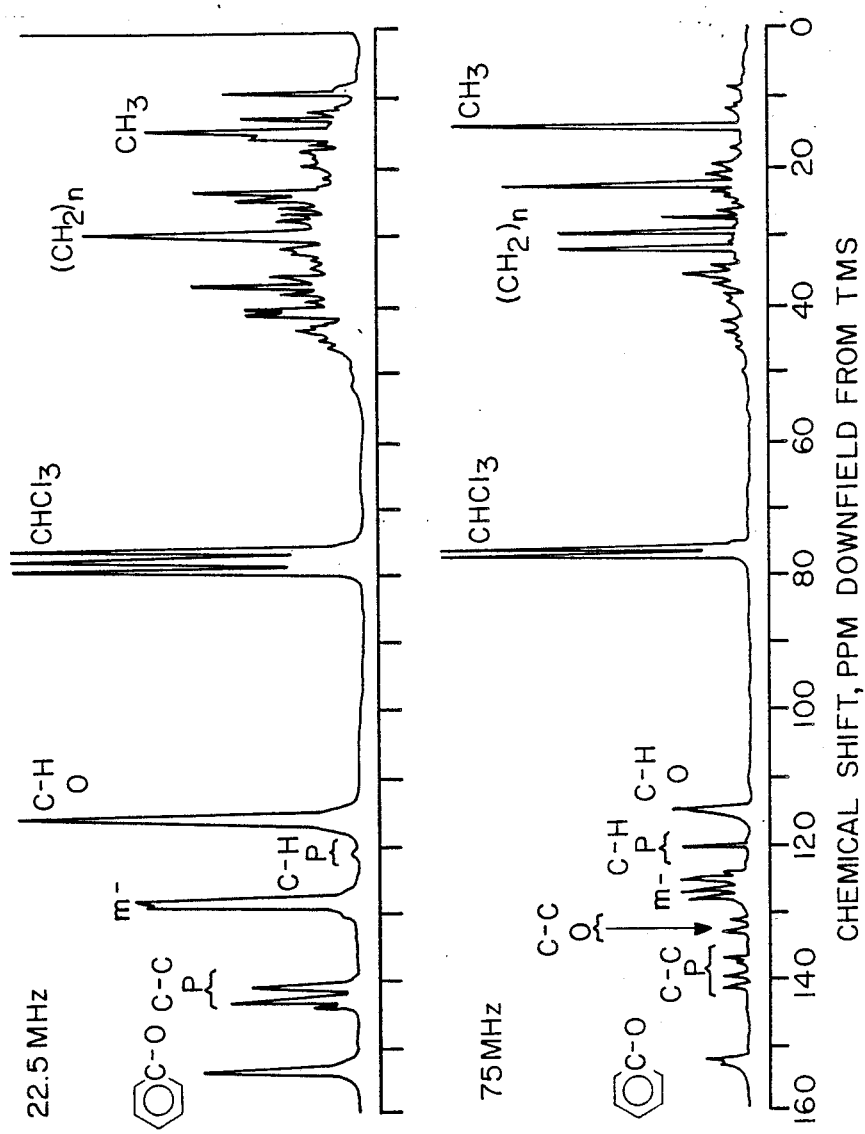

4,973,764

ALKYLPHENOLS AND DERIVATIVES THEREOF VIA PHENOL ALKYLATION BY CRACKED PETROLEUM DISTILLATES

This is a continuation of application Ser. No. 113,619 filed Oct. 26, 1987, now U.S. Pat. No. 4,914,246, which is a CIP of U.S. Ser. No. 922,877 Oct. 24, 1986, abandoned.

FIELD OF THE INVENTION

This invention relates to novel compositions of matter and methods of making the same. More particularly, this invention relates to the alkylation of phenols by olefinic components of cracked petroleum distillates to produce novel alkylphenols; and to derivatives of the alkylphenols.

As such the invention is related to the composition, separation and alkylation chemistry of olefinic cracked petroleum distillates especially of thermally cracked petroleum residua of high sulfur content.

The invention is particularly related to the chemistry of $C_8$ and higher alkylphenols. It is aimed at the preparation of semilinear alkylphenols derived by alkylating phenols with the largely linear olefin components of distillates derived by the high temperature thermal cracking of petroleum residua. Furthermore, the invention is concerned with the ethoxylation and propoxylation of alkylphenols, particularly of those derived from cracked petroleum distillates, especially coker distillates. The preparation of sulfate and sulfonate derivatives of the ethoxylated and propoxylated alkylphenol products is also described. Finally, the conversion of alkyl phenols to sulfurized metal phenate overbased detergents is discussed.

PRIOR ART VERSUS THE PRESENT INVENTION

The alkylation of phenols by olefins in the presence of acids to produce alkylphenols is a well known reaction. Indeed, alkylphenols are used in a wide variety of applications. For example, ortho alkylphenols are superior antioxidants compared to para alkylphenols as described in U.S. Pat. No. 3,929,654. The $C_8$ and higher branched alkylphenols are commercially used for the production of ethoxylated nonionic surfactants and their anionic sulfate and sulfonate derivatives. In this regard, see "Nonionic Surfactants" M. J. Schick, editor, M. Dekker, Inc., New York, NY, 1966, especially pages 44 to 85. For the chemistry of sulfate and sulfonate derivatives of alkylphenols, see also "Sulfonation Reactions", E. E. Gilbert, Interscience Publishers, New York, NY, 1965, particularly pages 378, 379, 350 and 297. The sulfation and sulfonation of ethoxylated alkylphenols is also described in U.S. Pat. Nos. 2,143,759; 2,106,716; 2,184,935; and 3,150,161. Other uses of alkylphenol derivatives include automotive lubricants additives. See, for example, "Lubricants and Related Products", D. Klamann, Verlag Chemie, Weinheim, W. Germany, 1984, particularly pages 181, 182, and 199.

As indicated above, alkylphenols are used in the preparation of surfactants. The most frequently used alkylphenol surfactant intermediates are t-octylphenol, t-nonylphenol and t-dodecylphenol. They are commonly prepared by the alkylation of phenol of diisobutylene, propylene trimer and propylene tetramer, respectively. These are highly branched alkylphenols, generally 95% being para substituted.

In contrast to the highly branched alkylphenols, there are known so-called linear alkylphenols. When produced via low temperature alkylation at about 80° C., these alkylphenols generally consist of close to a statistical mixture of ortho and para isomers, i.e., 66 to 33. These intermediates are prepared using linear alpha olefins as alkylating agents. Thus, U.S. Pat. No. 3,423,474 and Soviet Patent No. 882,995 disclose alkylations of phenols with alpha olefins as reactants. U.S. Pat. Nos. 3,312,734 and 3,432,567 disclose similar alkylations with cracked wax olefins. Also, U.S. Pat. No. 3,630,918 discloses the preparation of metal dialkyl dithiophosphate derivatives from alkylphenols derived from cracked wax olefins.

In U.S. Pat. No. 3,639,490 the alkylation of phenol or cresols by the olefinic components of a $C_6$ to $C_8$ catalytic gasoline stream to produce branched chain alkylphenol antioxidants is disclosed.

None of the foregoing references, however, teach the preparation of semilinear alkylphenols, i.e. alkylphenols derived from olefins comprising of major quantities of linear and minor quantities of branched olefins. There was no known olefinic feed for the preparation of such products.

As a part of the present invention it was discovered that thermally cracked petroleum distillates, particularly those derived from residual fuel oil by Fluid-coking and Flexicoking, contain unexpectedly major quantities of linear olefins and minor quantities of branched olefins. These olefins are valued below distillate fuel cost, because such cracked distillates have high concentrations of sulfur compounds and have to be extensively hydrogenated before they can be used as distillate fuels. The olefin components are converted to paraffins during such hydrogenations.

Furthermore, it was found in the present invention, that the sulfur compounds in such thermally cracked petroleum distillates are mostly inert aromatic, thiophene type compounds rather than catalyst inhibiting mercaptans.

A group preferred thermally cracked distillates, not previously considered as an alkylation feed, comprises naphtha and gas oil fractions produced in fluidized coking units. Integrated fluidized coking processes such as Fluid-coking and Flexicoking represent a superior refinery method for the conversion of residual fuel oil. The thermal cracking step of Fluid-coking and Flexicoking is identical. However, Fluid-coking does not utilize the residual coke produced with the coker distillate while Flexicoking employs the coke by-product for the production of low thermal value gas. A discussion of these processes is found in U.S. Pat. Nos. 2,813,916; 2,905,629; 2,905,733; 3,661,543; 3,816,084; 4,055,484 and 4,497,705 which are incorporated as references.

The preferred Fluid-coking and Flexicoking processes are low severity thermal cracking operations. Low severity is usually achieved by keeping the temperature relatively low in the range of 482° to 538° C. (900° to 1000° F.) while using a long residence, i.e., contact, time of about 20 to 60 seconds. Alternately, low severity can be achieved by using high temperatures, in the order of 538° to 705° C. (1000° to 1300° F.) and contact times of less than 5 seconds. In a long residence time operation, additional amounts of the desired olefin components can be produced by reinjecting the heavy gas oil distillate products into the cracking line.

The residual fuel feeds for the above coking processes are usually vacuum residua which remain after most of the crude petroleum is removed by refinery distillation processes. As such these residua typically possess boiling points above 565° C. (1050° F.) and have Conradson carbon contents above 15%. These residua contain most of the undesirable components of the crude, i.e. sulfur and nitrogen compounds and metal complexes. On coking much of the sulfur ends up in the distillate products. As a result of high temperature thermal cracking, major amounts of olefinic components are also formed and become major constituents of such distillates. In spite of their high monoolefin content such distillates generally were not considered as alkylation feeds because of their high sulfur and conjugated diolefin content. It was surprisingly found in the present invention that, in spite of the high sulfur content, the olefinic components of such feeds selectively react with added phenol to form semilinear alkylphenols.

The semilinear alkylphenols of the present invention differ from the highly branched and linear alkylphenols of the prior art in both the branchiness and the ortho versus para isomer distribution. They contain from about 1.4 to 2 branches per alkyl substituent on the average and ortho to para alkyl substituent ratios ranging from about 10/90 to 40/60.

DESCRIPTION OF THE FIGURES

FIG. 5 shows the separation of a 1-n-olefin - n-paraffin mixture from a $C_{16}$–$C_{19}$ Fluid-coker gas oil fraction by crystallization.

FIG. 6 shows the $^{13}C$ NMR spectrum of a highly branched dodecylphenol product of the prior art at the top and the spectrum of a comparatively semilinear dodecylphenol of the present invention at the bottom.

SUMMARY OF THE INVENTION

Figure 1:
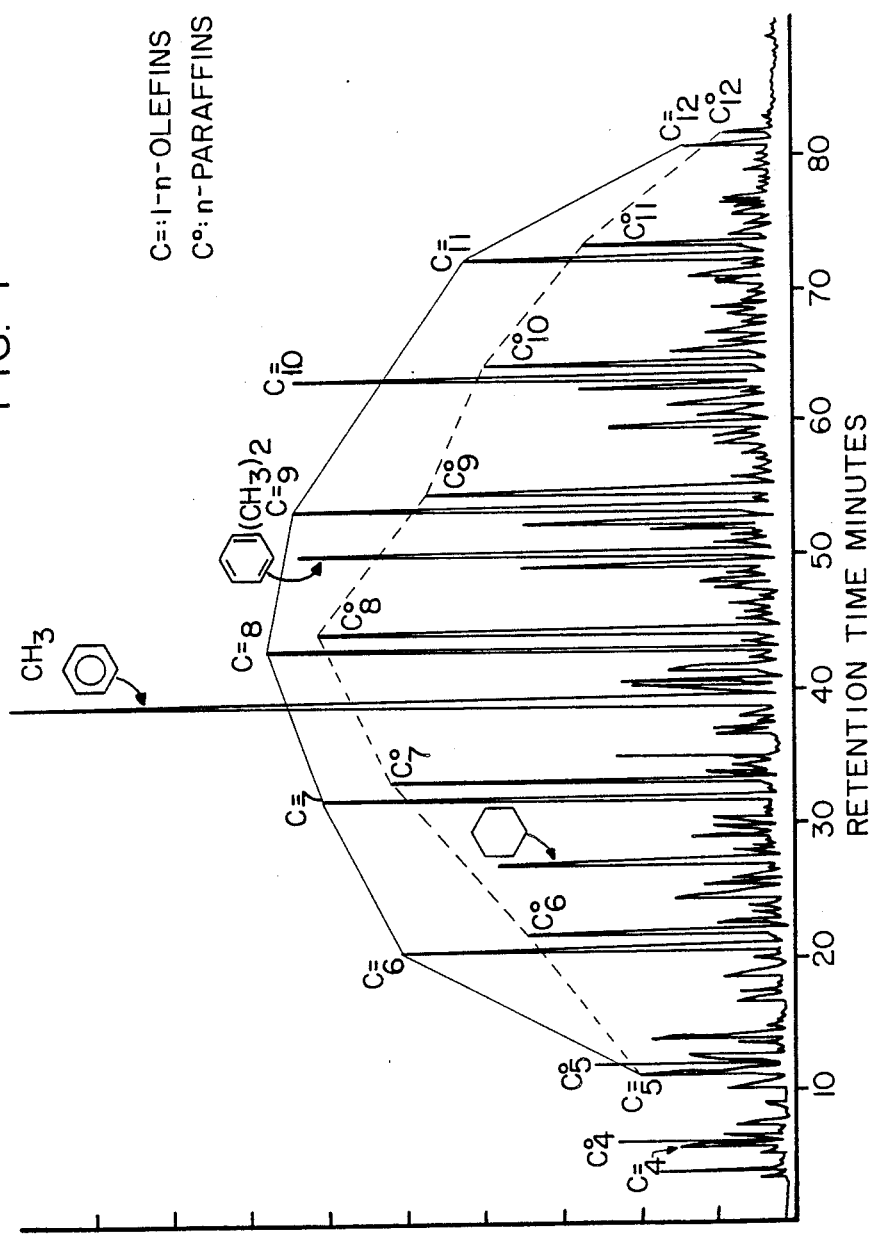
FIG. 1 shows the capillary gas chromatogram of a Fluid-coker naphtha feed in the $C_4$ to $C_{12}$ range, with an indication of the major 1-n-olefin and n-paraffin components.

In its simplest sense, the present invention is predicated on the discovery that phenols can be selectively alkylated with the olefin component of a thermally cracked sulfur containing petroleum distillate derived from residua in the presence of an acid catalyst to provide monoalkylphenols which have an average of less than two alkyl branches in the said alkyl group. The monoalkylphenols so obtained generally possess ortho to para ratios of about 10 ortho to about 90 para isomers to about 40 ortho to about 60 para isomers. Various derivatives of such alkylphenols are also contemplated.

Broadly stated then, the present invention is directed toward novel compositions of the following formula:

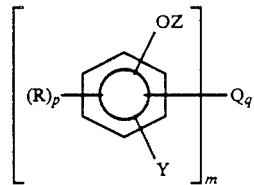

wherein

R is a $C_1$ to $C_{35}$, preferably $C_5$ to $C_{35}$, more preferably $C_8$ to $C_{29}$, most preferably $C_9$ to $C_{20}$ alkyl, $C_9$ and $C_{12}$ alkyl groups being specifically preferred; R is in an ortho and/or para position relative to the phenolic OZ group, with the proviso that at least one R is a higher $C_5$ to $C_{35}$ alkyl group said alkyl groups having an average of less than two but more than one branches therein, p is 1 or 2, preferably 1 with the proviso that if p is 1, the ratio of o- to p- R groups is from about 10 to 90 to about 40 to 60; preferably from about 20 to 80 to about 30 to 70;

Z is a phenolic hydrogen or a substituent member of the group consisting of Na, K, Ca, Mg, $(EO)_nH$, $(EO)_n(CH_2)_2SO_3M$, $(EO)_n(CH_2)_3SO_3M$ and $(EO)_nCH(CH_3)CH_2CH_2SO_3M$ wherein E is $CH_2CH_2$, $CH_2CH(CH_3)$, $CH(CH_3)CH_2$; M is H, Na, K, ammonium, Ca, Mg and n is 1 to 30; preferably 1 to 15;

Q is a bridging radical selected from the group consisting of S, $S_2$ and $CH_2$ with the proviso that if Q is S or $S_2$, Z is H, Ca or Mg and if Q is $CH_2$, Z is $(EO)_mH$; q, the number of bridging groups, is 0 to 15 with proviso that if Q is S or $S_2$, q is in the range of 1 to 5; m, the number of phenolic groups is 1 to 16, m being 1+q;

Y is selected from the group consisting of H and $SO_3M$ in which it is defined as above with the proviso that if Y is $SO_3M$, q is preferably 0 and Z is $(EO)_nH$;

The semilinear alkylphenol intermediates of the present invention are prepared according to the present process by reacting phenols with the olefin components of the high temperature cracking of sulfur containing residua, and are of the formula

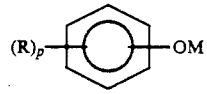

wherein the meaning of R and p is as defined before. M is H or Na, K, Ca, Mg, Co, Ni. Specifically, preferred semilinear alkylphenols are octylphenol, nonylphenol, undecylphenol, dodecylphenol. The preferred semilinear monoalkylphenol compositions possess o- to p- ratios of their alkyl groups in the range of about 10 to 90 to about 40 to 60.

In the preferred monophenol compositions, the value of Q is 0. In this case, the compounds generically are of the formula

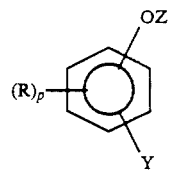

wherein OZ represents a phenolic group in which Z is selected from the group consisting of H, Na, K, Ca, Mg, $(EO)_nH$ and $(EO)_n(T)_{(t)}(SO_3)_u$ and in which E is selected from the group consisting of $CH_2CH_2$, $CH(CH_3)CH_2$ and $CH_2CH(CH_3)$, n is 1 to 30, T is selected from the group consisting of $CH_2CH_2$, $CH_2CH_2CH_2$, $CH(CH_3)CH_2CH_2$, t is 0 or 1, m is H, Na, K, ammonium, Ca, mg, Ni, Co, or Fe, and u is 0 or 1 provided that if t is 1, u also is 1; and Y is selected from the group consisting of H and $(SO_3)M$ in which M is as defined above; and R is selected from the group consisting of $C_5$ to $C_{35}$ branched alkyl groups having an average of about 1.4 to about 2 branches therein in an ortho and/or para relationship to the phenolic OZ group and in which p is 1 or 2 provided that when p is 1, the ratio of ortho to para isomers is between about 10 ortho to about 90 para to about 40 ortho to 60 para isomers, preferably from about 20 to 80 to about 30 to 70.

The present invention also is directed toward a method of preparing these compositions.

These and other features of the invention will become more readily understood upon a reading of the detailed description of the invention which follows.

DETAILED DESCRIPTION OF THE INVENTION

The alkylphenols of the present invention are prepared by reacting phenol with a hydrocarbon feed containing more than 15% monoolefins having $C_5$ to $C_{35}$ carbon ranges. These monoolefins contain from about 30 to 50% 1-n-olefin, 15 to 30% linear internal olefin and 30 to 45% monobranched olefins and have terminal to internal unsaturation ratios being in the range of from about 1.5 to 1 to about 4 to 1. Indeed, it is preferred that the hydrocarbon feed employed in the practice of the present invention be an olefin containing distillate fraction of thermally cracked hydrocarbons derived from petroleum residua. Consequently, specific mention is made hereinafter to olefin containing distillate fractions of thermally cracked residua; however, it will be appreciated that other feeds having substantially similar properties can be employed.

The preferred cracked distillates of the present feed contain relatively high amounts of organic sulfur compounds. The sulfur concentrations are preferably between 0.1% (1000 ppm) and 5% (50,000 ppm) more preferably between 0.5% (5000 ppm) and 4% (40,000 ppm). The prevalent sulfur compounds of the preferred feeds are aromatic, mainly thiophenic. Most preferably the aromatic sulfur compounds represent more than 90% of the total. In view of this characteristic of the feed, the present finding of selective phenol alkylation is surprising since thiophenes are highly reactive and tend to polymerize under acid conditions.

To summarize, the olefin-containing reactant used as a feed in the present invention will generally have from $C_5$ to $C_{35}$ carbon ranges. More preferably, the carbon range in such olefin-containing fractions will be from $C_8$ to $C_{29}$ and most preferably from $C_9$ to $C_{20}$. Additionally, it is particularly preferred in the practice of the present invention that greater than 25%, for example, 30% to 80% of the olefins in the feed be linear aliphatic olefins.

As indicated, the olefin feed is reacted with phenol. Normally at least one mole of phenol per mole of olefin will be employed; however, it is generally preferred to use excess phenol.

The reaction of phenol and the olefinic feed is conducted at temperatures sufficient to alkylate the phenol. In general these are temperatures of about 20° C. and 450° C. and preferably from about 20° C. to 50° C. more preferably from 80° to 130° C.

Importantly, the reaction is conducted in the presence of an effective amount of an acid catalyst. In general, the acid concentration in the reaction mixture will vary from about 1% to about 50% by weight and preferably from 5% to 25%.

Among the acid catalysts that are suitable in the practice of the present invention are strong acids such as sulfuric acid, phosphoric acid, phosphonic acid, sulphonic acid, inorganic polyacids, such as aluminosilicate clays, acidic cation exchange resins, such as sulfonic acids, based on crosslinked styrene, divinylbenzene polymers, boron trifluoride, hydrogen fluoride, tetrafluoroboric acid and other combined acids. Insoluble acid catalysts are preferred. The particularly preferred catalyst in the process of the present invention is a sulfonic acid derivative of an insoluble cross-linked styrene, divinyl resin.

It should be readily appreciated that reaction of phenols with linear olefins will lead to alkylphenol products which can be further alkylated to provide dialkylphenols. Formation of such dialkyl phenols can be suppressed, if desired, by employing a large excess of phenol reactant and employing relatively mild reaction conditions.

Also, as will be readily appreciated, the alkylphenol reaction products of the present process can be separated from unreacted feed components by standard separation techniques such as fractional distillation.

Another aspect of the present invention is the conversion of the alkylphenol products derived from cracked distillates. The most important type of conversion provides novel surfactants, preferably via ethoxylation and/or propoxylation. In another important reaction, such alkylphenols or their ethoxylated/propoxylated derivatives are reacted with propanesultone, butanesultone or sulfuric acid to produce sulfonate surfactants. In a different reaction, semilinear alkylphenols are converted to overbased automotive lubricant additives, preferably by reaction with sulfur and calcium oxide plus carbon dioxide. Furthermore, semilinear alkylphenols can be also employed to prepare demulsifier additives by reacting them with formaldehyde and ethylene oxide. The reaction of the present alkylphenols with sulfur dichloride provides an antioxidant for automotive lubricants. Metal derivatives of such compounds act as octane number improvers as disclosed in U.S. Pat. No. 4,536,192 by Braid et al. (assigned to Mobil Oil Corp.). Via another reaction with phosphorus pentasulfide, zinc dialkylaryl dithiophosphate lubricant additives are produced.

The processes converting the semi-linear alkylphenol intermediates of the present invention to useful products are carried out under prior art conditions, developed for highly branched alkylphenols. However, these further conversions of the present alkylphenols as a part of a multi-step process have a further advantage. In general, they produce higher boiling, less volatile products which can then be better separated from the unreacted cracked distillate components and alkylation by-products than the alkylphenol intermediates. The product impurities can be simply removed by distillation in vacuo.

Olefinic Thermally Cracked Feeds

The olefinic feed of the present process is a critical factor in producing the novel alkylphenols at a low cost. The preferred feed is produced by thermal cracking of petroleum residua.

Thermal cracking of petroleum residua produces hydrocarbons of more linear olefinic character than catalytic cracking does. It was found in the present invention that the percentage of olefins including 1-n-olefin components in thermally cracked petroleum distillates generally increases with increases in the cracking temperature. Therefore, the olefin containing distillate fractions derived from petroleum residua by high temperature thermal cracking processes are preferred feeds for alkylation of phenols in accordance with the present invention of the present process.

There are two main commercial processes for producing thermally cracked petroleum distillates from residua. They were reviewed by Jens Weitkamp in the journal, entitled Chem. Ing. Tech. No. 2, pages 101–107 in 1982. These processes are coking visbreaking, representing severe and mild cracking processes. The main coking processes are Flexicoking and Fluid-coking which produce the preferred distillate feeds of the present invention.

Suitable distillate feeds can be also prepared in thermal processes employing a plurality of cracking zones at different temperatures. Such a process is described in U.S. Pat. Nos. 4,477,334 and 4,487,686. Each of these thermal cracking processes can be adjusted to increase the olefin content of their products. Heavy gas oil distillates can be further cracked to increase the amount of lower molecular weight olefins.

The olefin containing distillate fractions of thermal cracking processes may be employed as feeds in the process of the invention without prior purification; however, these distillate fractions may optionally be treated prior to their use to reduce concentrations of aromatic hydrocarbons, sulfur and nitrogen compounds if so desired. For example, aromatic hydrocarbons and sulfur compounds can be selectively extracted from the olefin containing fraction by polar solvents. Mercaptan components can be removed with base. Nitrogen and sulfur compounds in general can be removed by use of absorption columns packed with polar solids such as silica, Fuller's earth, bauxite and the like. In the higher fractions, more than 90% of the sulfur compounds are present as thiophenic compounds, i.e., alkylthiophenes, benzothiophenes, etc. High temperature fixed beds of either bauxite or Fuller's earth or clay can be used to convert sulfur compounds to easily removable $H_2S$ with a concurrent isomerization of the olefin components.

The conjugated olefin components of the present feeds may be removed by prior mild hydrogenation or selective alkylation prior to use. The branched olefin components can be similarly removed e.g. by water, alcohol or acid addition. 1-n-Olefin components can be selectively reacted via hydroformylation or removed together with the n-paraffins by cocrystallization.

The cracked refinery distillate products, light and heavy naphthas and gas oils, are preferably further fractionated prior to use in the present process. The preferred broad carbon ranges of the thermally cracked feeds are from $C_5$ to $C_{35}$. A more preferred carbon range is from $C_8$ to $C_{29}$. The most preferred range is from $C_9$ to $C_{20}$. It is desirable to limit the carbon number range of any given distillate feed by efficient fractional distillation to five carbons, preferably three carbons and more preferably to one carbon to facilitate the separation of alkylphenol products of increased boiling range from the unreacted feedstock.

Specifically, preferred feeds are $C_9$ and $C_{12}$ cracked distillate fractions for the preparation of semilinear $C_9$ and $C_{12}$ alkylphenols, respectively. In case of very sharp distillate fractions within a single carbon range, the ratio of the different types of isomeric olefin components depends on the boiling range point.

The olefin content of the present cracked distillate feeds is about 15%, preferably above 30%, more preferably above 40%. The 1-n-olefins are preferably the major type components.

The main olefin reactant components of the present feeds are nonbranched Types I and II plus monobranched Types III and IV as indicated by the following formulas (R=hydrocarbyl, preferably non-branched alkyl):

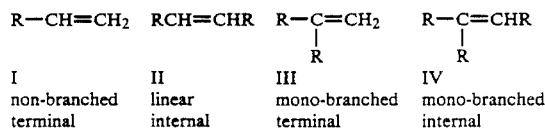

| $R-CH=CH_2$ | $RCH=CHR$ | $R-\underset{\underset{R}{\mid}}{C}=CH_2$ | $R-\underset{\underset{R}{\mid}}{C}=CHR$ |
|---|---|---|---|
| I | II | III | IV |
| non-branched terminal | linear internal | mono-branched terminal | mono-branched internal |

The concentration Type I olefins is preferably from about 30 to 50% of the total olefin concentration. Similarly, the percentage of Type II olefins preferably from about 15 to 30%. Type V olefins of formula $R_2C=CR_2$ are essentially absent.

The n-alkyl substituted Type I olefins, i.e. 1-n-olefins, are generally present in the highest concentration in these thermally cracked distillate feeds.

Alkylation Process of the Invention

The alkylation process of the present invention comprises reacting an olefinic cracked petroleum distillate feed, preferably produced from petroleum residua by high temperature thermal cracking and containing 1-n-olefins as the major type of olefin components and organic sulfur compounds, between 0.1 and 5% sulfur, more preferably between 0.5 and 4%, with phenol or cresol, preferably phenol, employing at least one mole of excess phenol per mole olefinic reactant, preferably in the liquid phase, at least one mole of excess phenol per mole olefinic reactant, preferably in the liquid phase, at temperatures between about 20° and 450° C., preferably from 20° to 150° C., more preferably from 80° to 130° C., in the presence of effective amounts of an acid catalyst, preferably a strong acid insoluble in the reaction medium, to produce alkylphenols as the major products, preferably a $C_8$ to $C_{30}$ semilinear monoalkylphenol and preferably including, in addition to said alkylation process step, the step of reacting the alkylphenol (a) either with an alkoxylating agent selected from the group consisting of ethylene oxide and/or propylene oxide to produce an ethoxylated and/or propoxylated alkylphenol nonionic surfactant and preferentially converting the said nonionic surfactant to a sulfonate surfactant derivative preferably by reacting it with propanesultone or butanesultone (b) or with a sulfoalkylating agent, preferably selected from the group consisting of propanesultone and butanesultone, to produce an alkylphenoxyalkanesulfonate surfactant (c) or with sulfur dichloride to produce a sulfurized alkylphenol oligomer antioxidant, largely o,o'-bis-alkylphenyl sulfide, preferentially converting said antioxidant to an overbased metal phenate detergent by reacting it with calcium hydroxide or magnesium hydroxide in the presence of $CO_2$.

(d) or with phosphorus pentasulfide to produce a di-alkylaryl dithiophosphate additive by reaction with zinc oxide (e) or with formaldehyde to produce an o,o'-bis-alkylphenyl methane dimer and other methylene bridged, oligomeric polyphenols and converting said polyphenols to their ethoxylated and/or propoxylated demulsifier derivatives by alkoxylation reactions with ethylene oxide and propylene oxide, respectively.

In the selective phenol alkylation process of the present invention the branched olefin components of the feed react at a faster rate than the linear olefins due to the better stabilization of the tertiary cation intermediates; e.g. in the case of p-alkylphenols:

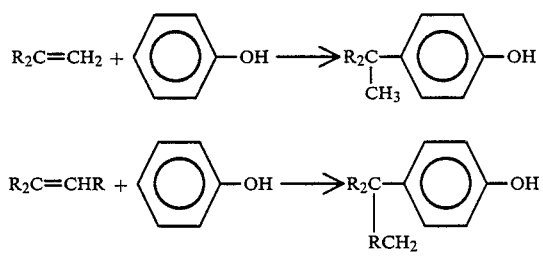

In the case of the less reactive linear olefins, isomerization is a common side reaction, particularly at low temperature. Thus, 1-n-olefins provide not only methyl but higher alkyl branched alkylphenols dependent on the reaction conditions, e.g.

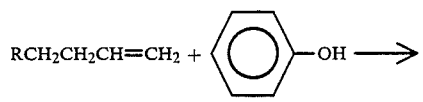

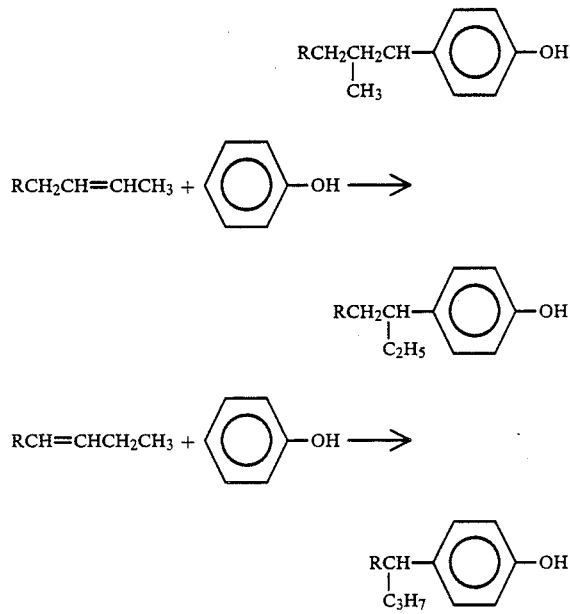

In general, branched olefins lead to t-alkylphenols while linear olefins provide s-alkylphenols. Thus the ratio of tertiary versus secondary alkylphenol products depends on the ratio of branched versus linear olefins reacted. The prior art isoalkylphenols derived from branched olefins are essentially all t-alkylphenols.

Branched olefins provide mostly para tertiary alkylphenols while linear olefins lead to mixtures of ortho and para secondary alkylphenols. 1-n-Olefins can give an o/p isomer mixture close to statistical i.e. a 66 to 33 o/p ratio. Thus the present process provides products of increasing o/p ratios with increasing olefin conversion of the cracked distillate feeds.

The monoalkylphenol products of the present process can be further alkylated to provide 2,4-dialkylphenols. For example, 1-n-olefins yield some of the following compounds:

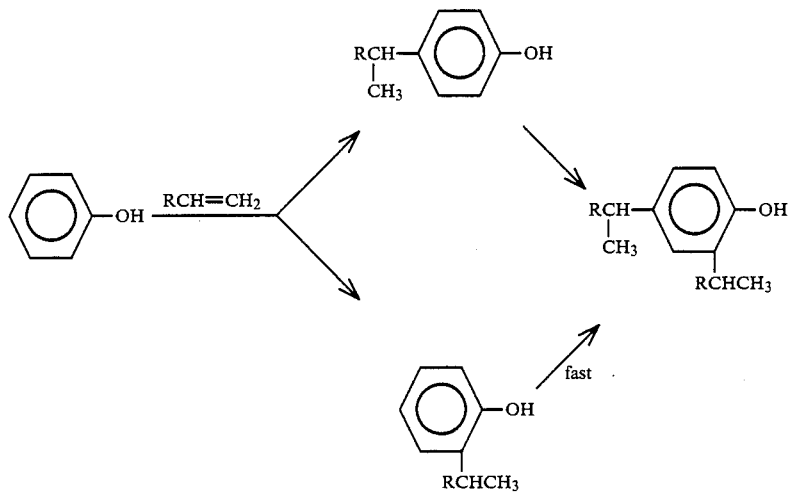

The formation of such dialkylphenols can be suppressed by employing a large excess of the phenol reactant and relatively mild reaction conditions.

One of the preferred catalysts of the present process is the sulfonic acid derivative of an insoluble crosslinked styrene divinylbenzene resin. This catalyst is preferably employed at temperatures below 150° C. to avoid decomposition and the formation of soluble sulfonic acids. Insoluble solid acids can be simply removed from the reaction mixture by filtration.

The alkylphenol products of the present process can be separated from the unreacted feed components by fractional distillation. However, it is important the all strong acids be removed or neutralized prior to distillation because at high temperature they can lead to a catalytic reversal of the alkylation reaction.

The alkylphenol products of the present invention, particularly the semilinear monoalkylphenols, can be derivatized to provide several different types of useful compositions. The monoalkylphenol intermediates can be further converted either prior to or after separation. Derivatization of the crude monoalkylphenol reaction products is often advantageous from the separations point of view since the derivatives are less volatile.

Alkoxylation

The alkylphenols can be ethoxylated and/or propoxylated in the presence of acid or base catalysts to provide alkylphenyl polyoxyethyl and/or polyoxypropyl alcohols. The first step of such base catalyzed alkoxylation reactions is much faster than those of the subsequent steps, e.g., in case of the p-alkylphenols.

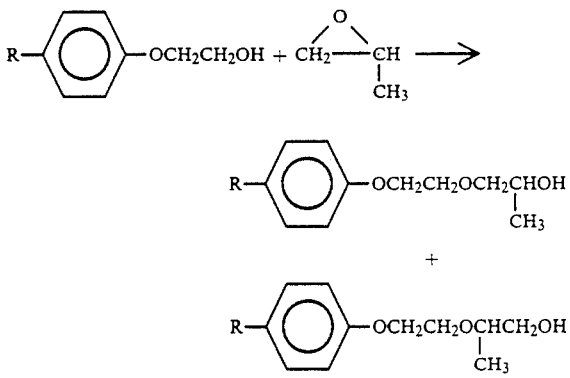

Thus, in an attractive process variant the alkylphenoxyethanol or alkylphenoxypropanol monoalkoxylation product is isolated by distillation and then further derivatized. Further ethoxylation of alkylphenoxyethanol results in a Poisson distribution of variously ethoxylated alkylphenol products. A similar behavior is observed in the propoxylation of alkylphenoxy-2-propanol. However, in case of propoxylation the isomeric product composition depends on the presence of base versus acid catalyst.

In general, the base catalyzed ethoxylation and propoxylation of the present alkylphenols is preferred be-

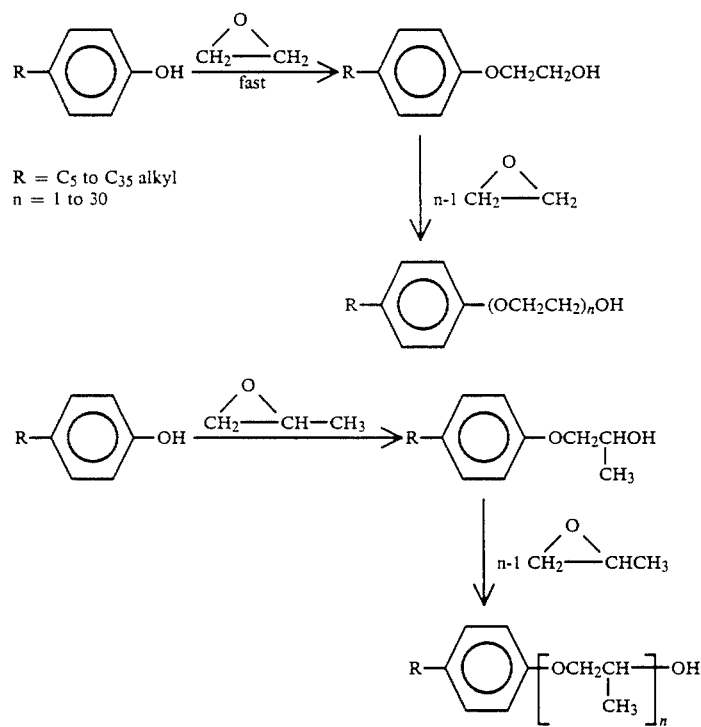

After the alkylphenol is monoethoxylated or propoxylated the high boiling products can be readily separated from the much lower boiling impurities by distillation.

The monoalkoxylated product can then be further reacted, e.g. ethoxylated or propoxylated. The acid catalyzed propoxylation is further discussed in the following because it forms mixtures of primary and secondary propoxylated alcohols; e.g.

cause of the high rate and selectivity of monoalkyoxylated product formation. Acids are poor catalysts of phenol-epoxide reactions. Selective formation of the monoalkoxylated products is particularly advantageous when the starting cracked olefin derived alkylphenol reactants are of a fairly broad boiling range and contain hydrocarbon and sulfur compounds as impurities.

While propoxylation in the presence of base catalysts essentially forms only secondary alcohols, in the presence of acid catalysts the major product isomer is the primary alcohol, e.g. 2-alkylphenoxyethoxylpropanol- the resulting sulfate sulfonate leads to the sulfonate as indicated by the following reaction scheme:

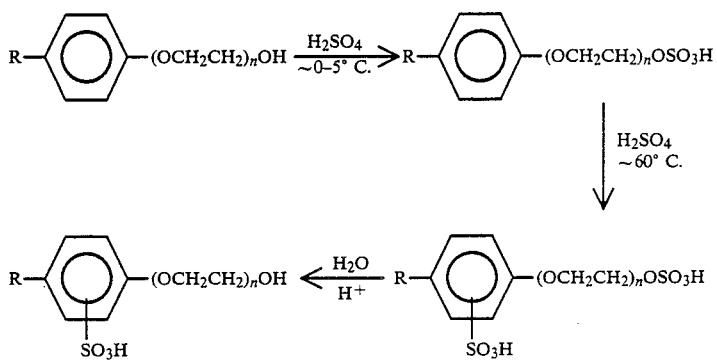

1. On further propoxylation in the presence of acid catalysts, the addition of primary and secondary propanol units continues. The generic formula of the resulting ethoxylated propoxylated alcohols is indicated in the following reaction scheme:

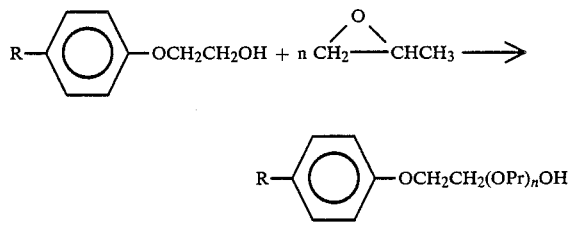

wherein Pr is $CH(CH_3)CH_2$ or $CH_2CH(CH_3)$. These products contain propylene moieties of different orientation and possess mainly alcohol end groups.

As base catalysts of alkoxylation sodium hydroxide and potassium hydroxide are frequently used. These catalysts react with alkylphenols to form the corresponding alkali phenolate. The latter in turn further reacts with the ethylene oxide or propylene oxide to produce a growing alkoxide moiety. Instead of alkali hydroxides, sodium or potassium may serve as precursors of the phenolate or alcoholate species. The molecular weight of the alkoxylated product is controlled by the phenol to ethylene oxide and/or propylene oxide ratio.

As acid catalysts of alkoxylation p-toluenesulfonic acid, silicon tetrafluoride, crosslinked polymeric sulfonic acids, antimony pentachloride, tin tetrachloride, trifluoromethanesulfonic acid and other strong acids can be used. Combinations of $BF_3$ with metal alkyls or hydrides e.g. of Al, Ti can be also employed. To avoid the polymerization of ethylene oxide, and/or propylene oxide, anhydrous systems are preferred.

Sulfation and Sulfonation

Cracked olefin derived alkylphenols and their ethoxylated/propoxylated derivatives both react readily with sulfuric acid and sulfur trioxide to form sulfates and sulfonates. Other sulfonating agents are complexes of $SO_3$ and sodium hydrogen sulfite. The latter is employed either in the Strecker reaction of halides and sulfates or addition reactions with olefinic derivatives. The ethoxylated alkylphenols are first sulfated under mild conditions and then sulfonated. Acid hydrolysis of the resulting sulfate sulfonate leads to the sulfonate as indicated by the following reaction scheme:

wherein the meaning of the symbols R and n is the same as before. Metal and ammonium slats of these sulfates and/or sulfonates are useful surfactants.

Sulfonate derivatives can be also prepared by reacting the alkylphenols and their ethoxylated/propoxylated derivatives with a sulfoalkylating agent. For example, the reaction of alkali metal derivatives with propanesultone on butanesultone lead to the corresponding sulfonate salts

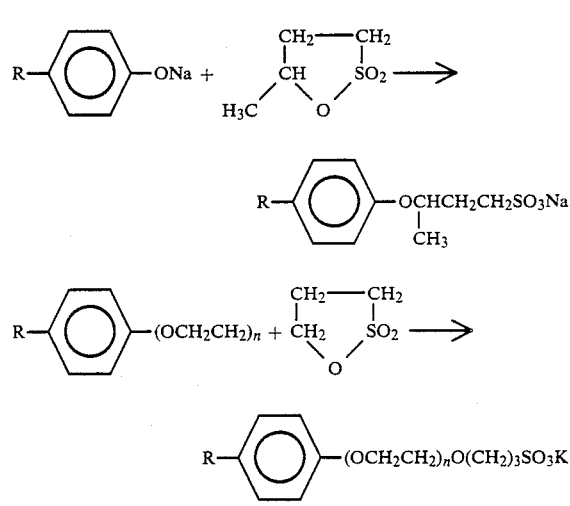

Other sulfoalkylating reagents are bromoethanesulfonate and vinylsulfonate salts.

Condensation with Sulfur Chlorides

Alkylphenols can be sulfurized primarily by technical sulfur dichloride, a mixture of $SCl_2$ and $S_2Cl_2$, preferably at about 80° C. to provide sulfur bridged condensation products having about 3 phenol moieties per molecule. For example, in the case of a nonylphenol dinonylphenol mixture the following product is formed:

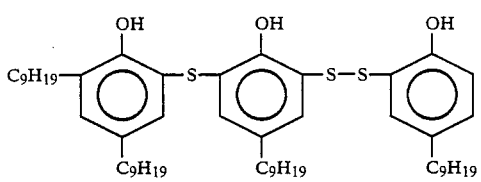

After the removal by the purging of all the HCl by-product and unreacted components from the reaction mixture, the product can be used as an antioxidant component of crankcase oil, an automotive lubricant. Similar products can also be used as additive intermediates.

As a preferred example, sulfurized 4-t-dodecylphenol is used for the preparation of an overbased detergent additive based on monoalkylphenols. Dodecylphenol is largely converted to the corresponding overbased calcium dodecylphenolate by reacting it in a higher alcohol solvent with elemental sulfur and calcium oxide in the presence of ethylene glycol and then carbon dioxide. Although the exact sequence of reactions is not known, the main course of the reaction can be indicated by the following scheme.

dodecyl group of the cracked olefin derived alkylphenol resulted in advantageously reduced viscosity and thus improved processability.

The overbased calcium dodecylphenolate product is used as a detergent additive component of marine engine oils and crankcase oils. As an additive it is acting not only as a detergent antioxidant but as a neutralizer of acidic oxidation by-products.

Overbased magnesium alkylphenolates can be also prepared and are useful as superior detergent additives. However, in their synthesis the key magnesium hydroxide reactant is to be derived from a magnesium alcoholate. For example, in the case of the overbased magnesium dodecylphenolate, the overall process scheme is the following:

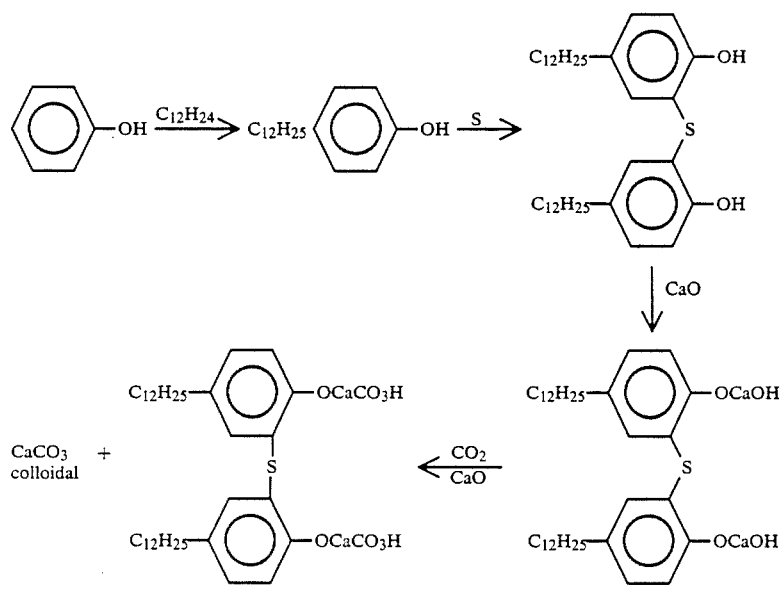

The viscosity of the i-dodecylphenol intermediate of the above scheme depends on the branchiness of the i-dodecyl group. A reduced viscosity is desired for the ease of processing. The reduced branchiness of the

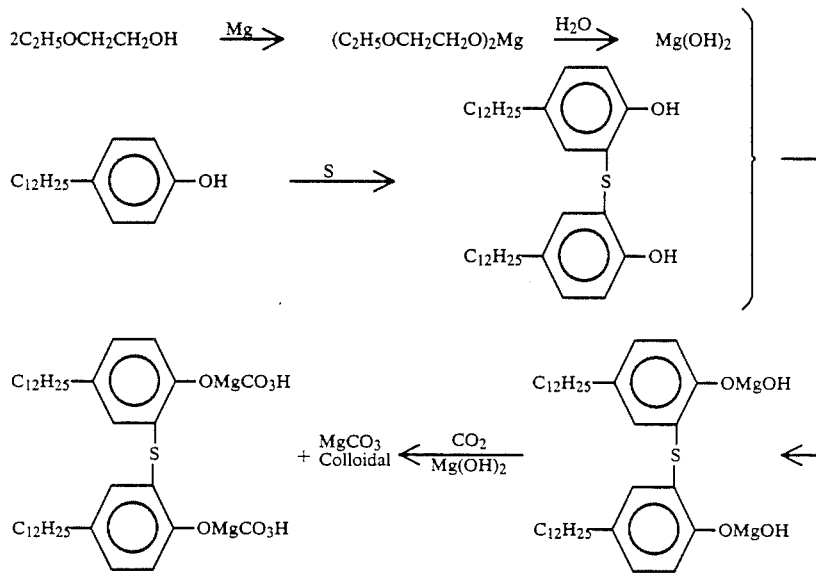

Condensation with Formaldehyde

Alkylphenols derived from cracked distillates are readily condensed with formaldehyde. The resulting methylene bridged condensation products are then ethoxylated and/or propoxylated, preferably in the presence of a base catalyst, to provide oligomeric surfactants useful as demulsifiers, fuel additives and coal slurry stabilizers. The reaction scheme is illustrated with nonylphenol in the following:

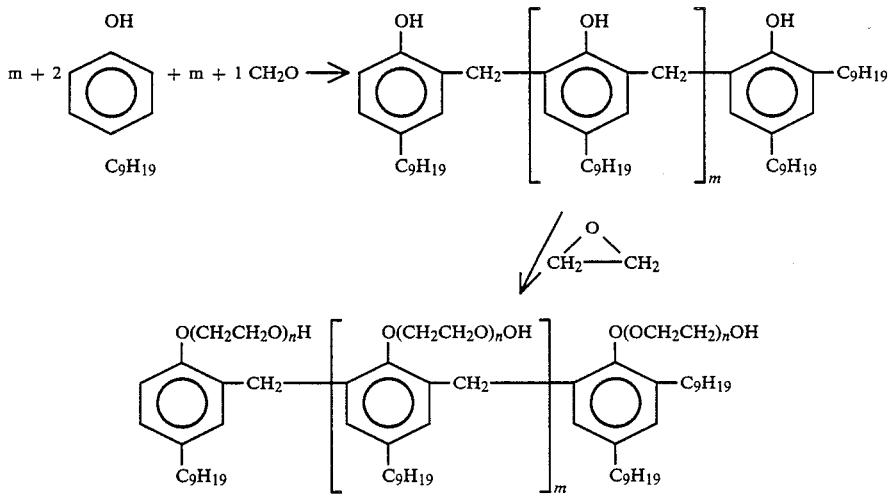

wherein $m$ is 0 to 15, preferably 1 to 10, $n$ is 1 to 30.

Reaction with Phosphorus Pentasulfide

Semilinear alkylphenols of the present invention are readily reacted with phosphorus pentasulfide via known methods. For example, the method described by Bencze in the journal "Schmierstoffe und Schmierungstechnik," No. 5, pages 4 to 16 in 1966, may be used. The resulting bis-alkylaryl dithiophosphoric acids are in turn converted to the corresponding zinc dialkyldithiophosphates as indicated by the following reaction scheme:

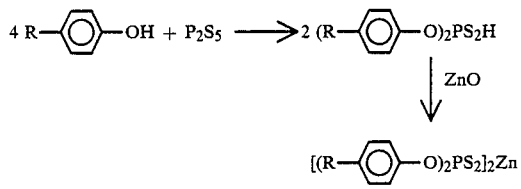

The zinc dialkyldithiophosphate products, which usually contain excess Zn as hydroxide, are high temperature antioxidants useful as lubricating additives.

Alkylphenol Derived Compositions

The ethoxylated and/or propoxylated semilinear alkylphenol compositions are also derived by alkylating phenols with the olefin components of thermally cracked distillates in the first step. They are of the formula $$(R)_p\!-\!\!\bigcirc\!\!-\!O(EO)_nH$$

wherein the meanings of R and p are as previously defined; E is $CH_2CH_2$, $CH(CH_3)CH_2$ and $CH_2CH(CHCH_3)$, preferably $CH_2CH_2$, n is 1 to 30, more preferably 1 to 15. Monoethoxylated compositions where n is 1 are specifically preferred:

$$R\!-\!\!\bigcirc\!\!-\!O(CH_2CH_2)_nOH$$

$$C_9H_9\!-\!\!\bigcirc\!\!-\!OCH_2CH_2OH$$

The most important derivatives of the present ethoxylated and/or propoxylated alkyl phenols are the sulfates and sulfonates. They are preferably of the formula $$(R)_p\!-\!\!\bigcirc\!\!\genfrac{}{}{0pt}{}{O(EO)_n(T)(SO_3)_uM}{(SO_3M)_r}$$

wherein the meaning of R, p, EO and n is the same as previously defined;

T is $CH_2CH_2$, $CH_2CH_2CH_2$, $CH(CH_3)CH_2CH_2$, preferably $CH(CH_3)CH_2CH_2$; t is 0 or 1; M is H, Na, K, Ca, Mg, Ni, Co, Fe, preferably H and Na; u is 0 or 1 with the proviso that if t is 1, u must be also 1, and r is 0 or 1.

A preferred subgenus of the above compounds consists of sulfate derivatives of ethoxylated alkyphenols of the formula is a precursor of the ethoxylated sulfonate of the formula

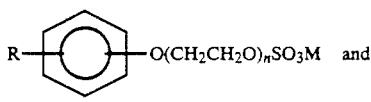

The sulfate sulfonate of the above formula is a precursor of the ethoxylated sulfonate of the formula

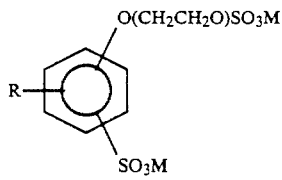

wherein the meaning of the symbols is the same.

Another preferred type of sulfonate derivative of the present ethoxylated monoalkylphenol is of the formula

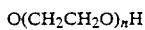

wherein the generic meaning of the symbols, R and T is the same. n is 1 to 35 preferably 1 to 15. A specific preferred group of sulfonates of this type is

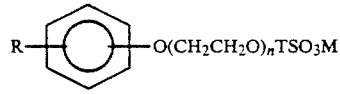

The mono ethoxylated sodium sulfonate compound is specifically preferred:

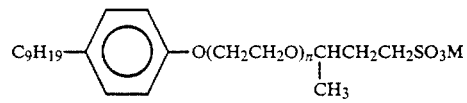

Another type of composition derived from the present semilinear alkylphenols comprises sulfur bridged antioxidant compounds of the formula

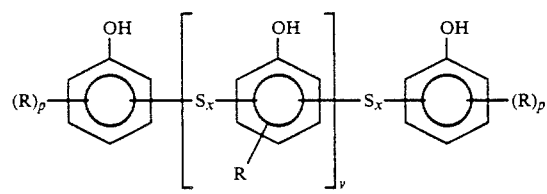

wherein the meaning of R and p is the same, R is more preferably $C_8$ to $C_{12}$, most preferably $C_9$ alkyl, the bridging sulfur groups are in ortho para positions relative to the phenolic hydroxyl, mostly ortho, x is 1 or 2, mainly one and v is 0 to 6, preferably 1 to 3. The sulfur bridged semilinear nonylphenol, having an average value of v between 0 and 2, preferably equaling 1, is specifically preferred.

Sulfur bridged overbased calcium and magnesium phenate derivatives of semilinear monoalkylphenols are detergent additives of a distinct type. They contain structural units of the formula

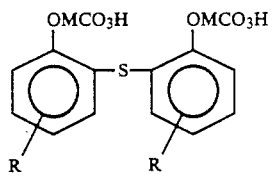

wherein the meaning of R is a $C_5$ to $C_{35}$ alkyl, preferably, a $C_9$ to $C_{18}$ alkyl, most preferably $C_{12}$ alkyl; M is Ca or Mg, preferably Ca.

Methylene bridged semilinear mono alkylphenols and their ethoxylated and/or propoxylated derivatives represent another subgenus of the present compositions. They are of the formula

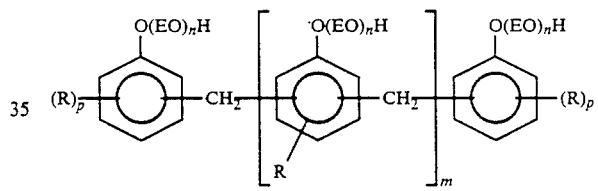

wherein the meaning of R is a $C_5$ to $C_{35}$ alkyl, preferably a $C_8$ to $C_{15}$ alkyl, most preferably a $C_9$ alkyl, in an ortho and/or para position relative to the phenolic group. The bridging methylene groups are in an ortho or para, mostly ortho, position relative to the phenolic group, p is 1 or 2, preferably 1, m is 0 to 15, preferably 1 to 10, E is $CH_2CH_2$, $CH_2CH(CH_3)CH_2$ preferably $CH_2CH_2$, n is 0 to 30, preferably either 0 to 30.

Bis-alkylaryl dithiophosphate antioxidant additive derivatives of the present semilinear monoalkylphenols form another subgenus of the formula

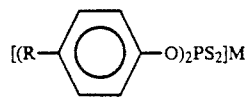

wherein R is $C_5$ to $C_{35}$ preferably $C_8$ to $C_{12}$ alkyl, in an ortho and/or para position relative to the phenolic oxygen, M is H, $(Zn)_{\frac{1}{2}}$, ZnOH, preferably $Zn_{\frac{1}{2}}$.

EXAMPLES

In the following, examples are provided to illustrate the present process of phenol alkylation and its products, without limiting invention. As an introduction to the examples the cracked distillates alkylating reactants are described. The composition of these reactants is a distinctive feature of the present invention.

Cracked Distillate Feeds

It was disclosed in the specification that the key factor in producing the highly olefinic reactant feed of the present invention is high temperature thermal cracking. Another factor is the origin and prior treatment of the petroleum residua to be cracked. The presence of the major 1-n-olefin components of the cracked distillates depends on the presence of normal alkyl groups in the crude oil. These olefins are formed by the cracking and dehydrogenation of n-alkyl aromatics and n-paraffins.

In the past the molecular structure of neither the petroleum residua nor the thermally cracked distillates was known. Thus the desirable characteristics of the present distillate feeds were not recognized. An important step in the present invention was the structural analysis of the complex distillate feeds by high resolution capillary gas chromatography (GC) magnetic resonance spectroscopy (NMR) and combined capillary gas chromatography/mass spectrometry (GC/MS).

The distillate fractions used as feed in the present invention were derived by the Fluid-coking of vacuum residua produced from Northwest American crude. Other distillate feeds, derived from Arabian crude in a Flexicoking unit, had similar compositions. The composition of these feeds in a wide carbon range is described in U.S. patent application Ser. No. 914,802, filed on Oct. 4, 1986 and now allowed. This application is incorporated by reference.

The composition of the $C_4$ to $C_{12}$ coker naphtha distillate was analyzed by GC using a temperature programmed 50 m column. The key components of the mixture were identified by GC/MS, with the help of standards as required. The gas chromatogram obtained is shown in FIG. 1 with symbols indicating the 1-n-olefin and n-paraffin components of various amounts. In the $C_6$ to $C_{12}$ range the 1-n-olefin to n-paraffin ratios range from about 1.1 to 2.1. The 1-n-olefins are the largest single type of compounds.

Lower cracking temperatures result in decreased olefin/paraffin ratios. For example, delayed coking which is carried out at a lower temperature than fluid coking gives distillates of lower ratios. An analysis of a naphtha fraction from a delayed coker gave an average of 0.3 1-n-olefin/n-paraffin ratio.

Figure 2:
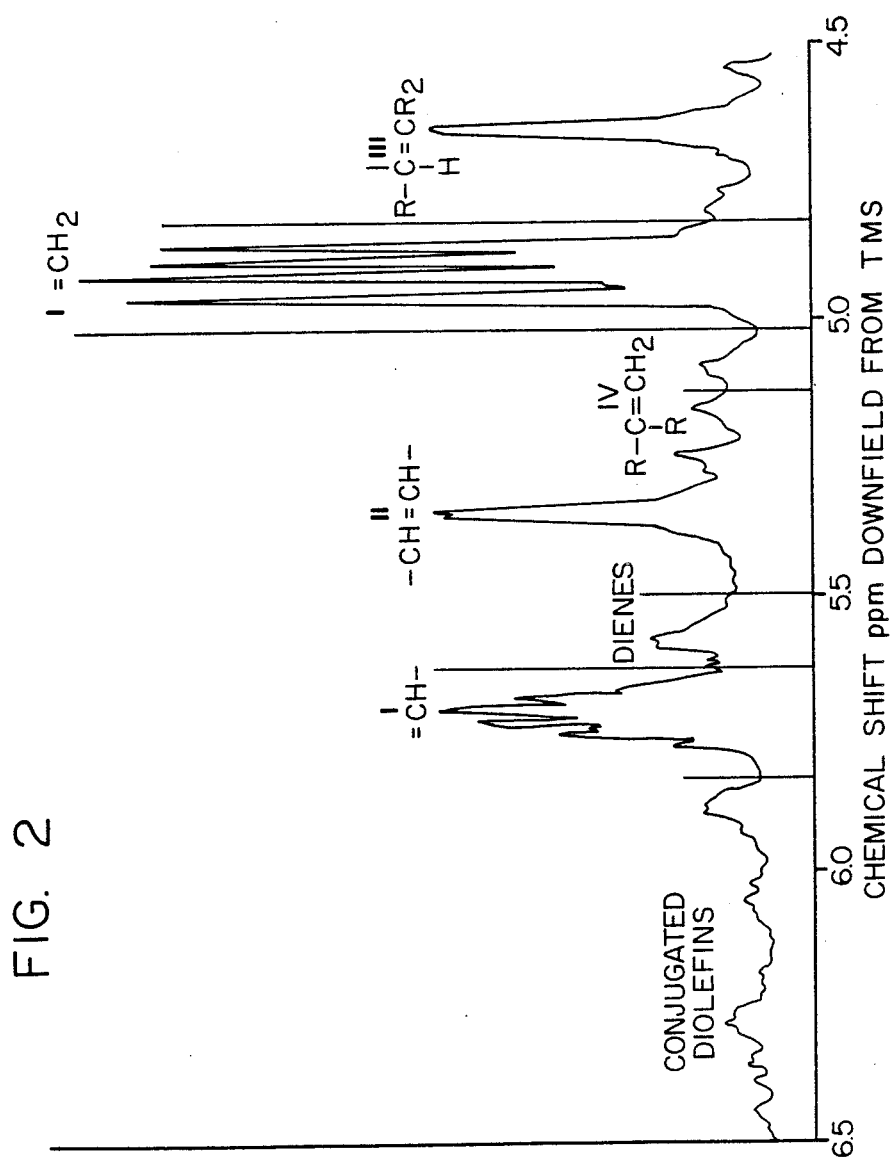
FIG. 2 shows the 400 MHz proton nuclear magnetic resonance spectrum of the olefinic protons of Fluid-coker naphtha feed, with an indication of the chemical shift regions of various types of olefins.

The broad $C_3$ to $C_{12}$ coker naphtha fraction was fractionally distilled, using a column equivalent to 15 theoretical plates with reflux ratio of 10, to produce distillates rich in olefins and paraffins of a particular carbon number. Selected fractions were studied by proton NMR using a JEOL GX 400 MHz spectrometer. FIG. 2 shows the NMR spectrum of the olefinic region of the naphtha with an indication of the chemical shift regions assigned to the vinylic protons of various types of olefins. A quantitative determination of the olefinic protons of the various types of olefins was used to estimate olefin linearity. The relative mole percentages of olefins of varying carbon numbers were calculated on the basis of amounts of the different types of olefinic protons. The results of these calculations and the boiling ranges of the fractions are shown in Table I.

The data of Table I show that the Type I olefins, i.e., monosubstituted ethylenes, are the major type of olefins in all the distillate fractions as well as in the starting $C_4$–$C_{12}$ naphtha. The percentage of Type I olefins in the distillation residue is, however, reduced to less than half of the original. It is assumed that this result is due to 1-n-olefin conversion during the high temperature distillation. Minor variations, between 32 and 50%, are also observed in Type I olefin content of distillate cuts.

The second largest olefin type present in the naphtha and its distillate consists of 1,2-disubstituted ethylenes. The percentage of these Type II olefins varies between 18 and 26%. Most, if not all, of these olefins are linear internal olefins.

Type III olefins, i.e., 1,1-disubstituted ethylenes were found to be present in amounts ranging from 12 to 17%. The major olefins of this type were 2-methyl substituted terminal olefins. Their branching occurs mostly at the vinylic carbon.

Type IV olefin, i.e., trisubstituted ethylenes, were the smallest monoolefin components of these distillates. Their relative molar concentration is in the 6 to 12% range.

Type V olefins, i.e., tetrasubstituted ethylenes, could not be determined by proton NMR.

Finally, Table I also lists small but significant quantities (8–16%) of conjugated diolefins. The amounts listed for these olefins are approximate because conjugated olefins may have a different number of vinylic hydrogens per molecule dependent on the site of conjugation and the presence of branching at vinylic sites.

The NMR spectra of naphtha fractions were also analyzed in the area of aromatic and paraffinic protons to estimate the amounts of olefins. From the percentage distribution of various types of hydrogens and the elemental analyses of these fractions, the weight percentage of various types of compounds was estimated.

The type I olefins, mostly 1-n-olefins were estimated to be present in these fractions in the range of 18.7 to 28.3%. These percentages depend on both the carbon number and the particular usually narrow boiling range of the olefinic fractions studied.

In the $C_6$ to $C_{10}$ range these values for the Type I olefins approximately correspond to the values obtained for 1-n-olefin by GC.

The total olefin content of these fractions is in the 47 to 62% range as determined by NMR. It is noted that the conjugated diolefins are included in this percentage

TABLE I

| Relative Amounts of Various Types of Olefins in Fluid Coker Naphtha Determined by 400 MHz Proton Magnetic Resonance Spectroscopy | | | | | | | | | | | |
|---|---|---|---|---|---|---|---|---|---|---|---|
| Naphtha Carbon No. | Mole Percentage Distribution of Various Types of Olefins | | | | | | | | | | |
| Boiling Point, °F. | $C_4$–$C_{12}$ | $C_5$ | $C_6$ | $C_7$ | $C_8$ | $C_8$ | $C_9$ | $C_{10}$ | $C_{11}$ | $C_{12}$ | Residue |
| Initial: | — | 80– | 140– | 195 | 245– | 254– | 293– | 335– | 374– | 410– | 425– |
| Final: | 410 | 100 | 150 | 205 | 257 | 262 | 30 | 359 | 390 | 425 | — |
| Olefin I: —CH=$CH_2$ | 37 | 31 | 50 | 42 | 36 | 32 | 44 | 43 | 39 | 36 | 16 |
| II: —CH=CH— | 20 | 25 | 18 | 25 | 26 | 26 | 22 | 22 | 23 | 28 | 28 |
| III: —C=$CH_2$ | 17 | 13 | 15 | 14 | 22 | 22 | 14 | 14 | 12 | 11 | 15 |
| IV: —C=CH— | 12 | 22 | 10 | 8 | 6 | 07 | 08 | 12 | 10 | 11 | 21 |
| Conjugated Diolefin[a] | 14 | 10 | 8 | 11 | 11 | 13 | 12 | 15 | 16 | 14 | 20 |

[a]The conjugated diene values are only approximate.

since they are converted to monoolefins under hydroformylation conditions or by a prior mild hydrogenation. Due to differences in the boiling points of olefin isomers, the relative proportion of linear versus branched olefin components is of course somewhat dependent on the boiling range of the feed. The table also shows significant and increasing amounts, up to 25%, of aromatic components in the various naphtha fractions. The aromatics are mostly hydrocarbons, i.e. alkylbenzenes and naphthalenes, but also contain significant amounts of alkylthiophenes and benzothiophenes. In the higher carbon fractions most of the sulfur is in the form of these heteroaromatic compounds.

Table II shows the elemental composition of Billings Fluid-coker naphtha fractions. Most importantly, the data of the table indicate a high percentage of sulfur. Surprisingly, in the $C_8$ and higher fractions, little of this sulfur is in the form of mercaptans. According to GC/MS, most of the sulfur of the $C_8$ to $C_{12}$ fractions is in the form of alkylthiophenes.

In the present examples, the $C_8$ and $C_9$ fractions of Billings Fluid-coker naphtha were used as alkylating feed. The $C_4$ to $C_{12}$ naphtha and $C_9$ to $C_{16}$ light gas oil fractions overlap. A $C_{12}$ fraction of Billings Fluid-coker light gas oil was also employed in an example.

Similar characterizations were performed on a light coker gas oil produced by the same Fluid-coking unit from which the coker naphtha was taken.

Figure 3:
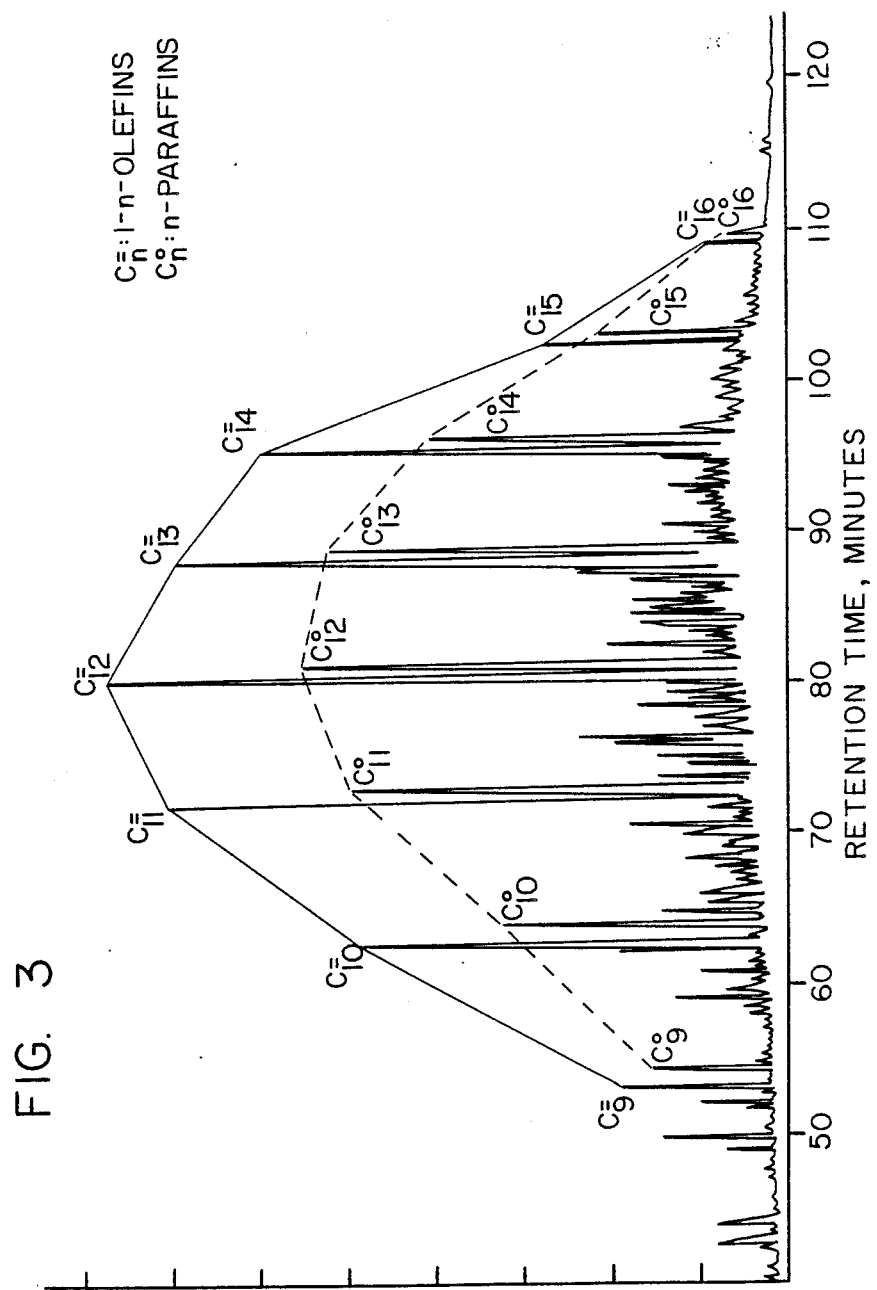
FIG. 3 shows the capillary gas chromatogram of the light Fluid-coker gas oil feed in the $C_9$–$C_{15}$ range, with an indication of the major 1-n-olefin and paraffin components.

FIG. 3 shows the capillary GC of the light gas oil in the $C_9$ to $C_{16}$ range. About 90% of the components are in the $C_{10}$ to $C_{15}$ carbon range. The $C_{11}$ to $C_{13}$ components are particularly large. Obviously, there is some overlap between this composition and that of the broad cut naphtha.

As it is indicated by the symbols of the figure, the main components are the 1-n-olefins and the n-paraffins. In general, the concentrations of the 1-n-olefins are greater than those of the corresponding paraffins. The 1-n-olefin to n-paraffin ratio is apparently maintained with increasing carbon numbers.

The light gas oil fraction was fractionally distilled to produce narrow cut distillates of a particular carbon number.

The light gas oil and these fractions were also studied by proton NMR. A quantitative analysis showed that this gas oil is highly olefinic with a strong aliphatic character in that 88.2% of the hydrogens in the mixture are on saturated carbons, 6.2% on olefinically unsaturated carbons and only 5.6% on aromatic rings.

Selected distillate cuts of the light gas oil were also analyzed by NMR in a similar manner. The distribution of their vinylic hydrogens was particularly studied to determine the relative amounts of the various types of olefins present. The results are summarized in Table III.

The data of Table III show that the relative olefin percentages of the distillate cuts vary. However, the percentage of the Type I olefins, including the desired 1-n-olefins, is generally more than a third of the total. The type I and II olefins combined, which includes all the linear olefins represent more than 55% of the total. The vinylically branched olefins are present in less than 35% amounts. The percentages of the conjugated diolefins are included in the table since they are converted to monoolefins during hydroformylation. However, the diene structures are uncertain and as such of approximate values.

Type III also shows the distribution of olefin types in case of four narrow cut $C_{12}$ distillate fractions. As expected varying amounts of the different types of olefins of different boiling points were found to be present. Thus the proportion of the Type I olefins changed from 45.5 to 33.8%.

From the distributions of various types of olefinic hydrogens, the weight percentages of the various types of olefins were estimated. The estimate of total olefins including dienes is between 50.4 and 61.7%. It is noted that the 61.7% value is for the $C_{16}$ fraction which was distilled with decomposition. As a result of cracking this fraction contained not only $C_{16}$ but lower molecular weight olefins as well. In the case of the $C_{12}$ range, four narrow cut fractions were analyzed to determine changes in the proportion of different types of compounds. Only moderate changers were found in total olefin concentration (45.5 to 54.4%).

To illustrate the detailed composition of the present gas oil feeds and to show the effect of polar adsorbents on separations, more detailed data are provided on a narrow $C_{12}$ fraction on the basis of GC/MS analyses. Such a cut cannot be separated on a nonpolar (boiling point) methylsilicone GC column. However, it was found that a highly polar type CP Sil 88 column (with a cyanopropylated silicone stationary phase) separated the various types of components according to their polarity.

TABLE II

Elemental Analyses of Distillate Fractions of Fluid Coker Naphtha

Carbon Hydrogen Sulfur and Nitrogen Content of Naphtha and its Fractions

| Naphtha Carbon Number | $C_4$–$C_{12}$ | $C_5$ | $C_6$ | $C_7$ | $C_8$ | $C_9$ | $C_{10}$ | $C_{11}$ | $C_{12}$ | Residue |
|---|---|---|---|---|---|---|---|---|---|---|
| Boiling Point, °F.: Initial | — | 80– | 140– | 195– | 245– | 290– | 335– | 374– | 410– | 425– |
| Final | 410 | 100 | 150 | 205 | 257 | 300 | 350 | 390 | 425 | — |
| Carbon, % | | | 85.64 | 85.81 | 85.83 | 86.10 | 86.41 | 86.11 | 85.98 | 85.23 |
| Hydrogen, % | | | 14.39 | 14.01 | 13.49 | 13.18 | 12.95 | 12.39 | 12.33 | 10.75 |
| Mercaptan Sulfur (SH), ppm | 600 | 1770 | 850 | 450 | 80 | 20 | 60 | 30 | 100 | 490 |
| Total Sulfur, ppm | 8900 | 1700 | 1300 | 2200 | 5100 | 5900 | 8800 | 12,000 | 13200 | — |
| Total Nitrogen, ppm | 159 | 141 | 46 | 25 | 45 | 158 | 134 | 135 | 136 | 1022 |
| % SH (100 SH/Total) | 6.74 | 100 | 65.38 | 20.45 | 1.57 | 0.34 | 0.68 | 0.25 | 0.76 | |
| Total Sulfur Compounds, % | | 0.40 | 0.36 | 0.71 | 1.86 | 2.42 | 3.99 | 5.96 | 7.14 | |

*The percentages of sulfur compounds in the various distillate fractions were calculated, assuming that they contain 2 carbon less per molecule than the hydrocarbon compounds of they fraction of a certain carbon number.

TABLE III

Relative Amounts of Various Types of Olefins in Light Fluid Coker Gas Oil Determined by 400 mHz Proton Magnetic Resonance Spectroscopy

| Gas Oil Carbon Number | $C_9$–$C_{16}$ | $C_9$ | $C_{11}$ | $C_{12}$ | $C_{13}$ | $C_{14}$ | $C_{15}$ | $C_{16}$ | Narrow $C_{12}$ Cuts | | | |
|---|---|---|---|---|---|---|---|---|---|---|---|---|
| Boiling Point, °F. Initial | 293 | 335 | 365 | 405 | 442 | 475 | 505 | 525 | 405 | 412 | 415 | 423 |
| Calcd. for 1 Atm. Final | 307 | 345 | 385 | 425 | 454 | 485 | 522 | 535 | 412 | 415 | 423 | 425 |
| Olefin I: —CH=$CH_2$ | 42 | 37.1 | 43.6 | 40.0 | 38.5 | 43.5 | 44.0 | 37.9 | 43.4 | 45.5 | 42.5 | 33.8 |
| II: —CH=CH— | 22 | 16.4 | 16.8 | 22.0 | 17.3 | 21.2 | 21.6 | 16.2 | 19.6 | 17.5 | 20.3 | 23.4 |
| III: —C=$CH_2$ | 16 | 16.4 | 12.3 | 13.4 | 18.7 | 16.1 | 12.2 | 18.6 | 15.6 | 12.3 | 12.0 | 14.5 |
| IV: —C=CH— | 7 | 18.3 | 15.9 | 12.7 | 15.5 | 9.1 | 13.1 | 15.9 | 9.5 | 14.7 | 14.0 | 15.1 |
| Conjugated Diolefins | 14 | 11.8 | 11.3 | 11.9 | 10.1 | 10.1 | 9.1 | 11.3 | 11.9 | 9.9 | 11.2 | 13.2 |

[This column is particularly suitable for the analysis of high boiling fractions since it has a high use temperature limit (about 275° C.)]. These components could then be largely identified via GC/MS studies. Two capillary GC traces with the groups of components identified are shown by FIG. 4.

The effluent of the above polar capillary column was split and led to a flame ionization and a sulfur specific detector. The chromatogram of the flame ionization detector shows the distribution of the organic compounds according to polarity in the lower part of the Figure. The upper chromatogram produced by the sulfur specific detector shows the elution of the sulfur compounds in the order of their polarity.

The lower GC of FIG. 6 shows good separation of the aliphatic, monoaromatic and diaromatic hydrocarbon components of the $C_{12}$ fraction. With the help of GC/MS the aliphatic components could be broken down to paraffins, olefins plus diolefins. Their percentages were 18.6 and 50.5%, respectively. The monoaromatics included alkylbenzenes, naphthenobenzenes and trace amounts of alkylthiophenes. The total amount of monoaromatics was 28.2%. The main diaromatic compounds were indene, nephthalene and benzothiophene.

Figure 4:
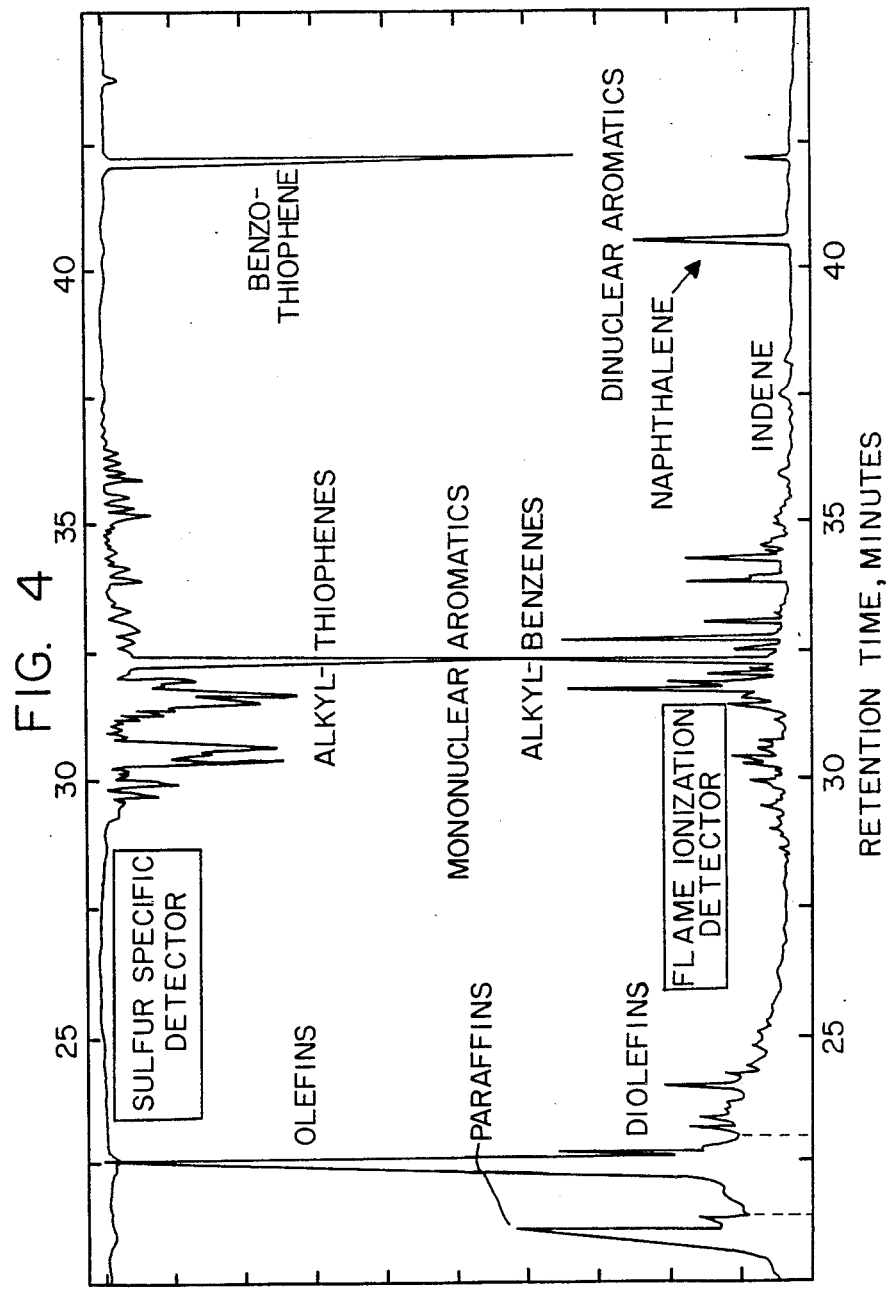
FIG. 4 shows the capillary gas chromatogram on a highly polar column of a $C_{12}$ fraction of light Fluid-coker gas oil, with separation of various types of aliphatic and aromatic components and sulfur compounds.

The upper, sulfur specific GC of FIG. 4 shows that essentially all the sulfur compounds of the $C_{12}$ fraction were aromatic. The majority were alkyl thiophenes. Benzothiophene was also present in significant amounts. A similar analysis of the $C_{14}$ fraction showed an even better separation of the components according to their polarity. In this case the distribution of the aliphatic components was similar but the major aromatic components were dinuclear: methylnaphthalenes and methylbenzothiophenes.

The distillate fractions of light gas oil were also analyzed for elemental composition, particularly for sulfur and nitrogen compounds and mercaptans. The data obtained are summarized in Table IV.

The percentages of carbon and hydrogen were rather well maintained with increasing molecular weights. They indicate that the aliphatic character of the gas oil was fairly maintained. The total sulfur content remained at about 1% in the $C_9$ to $C_{12}$ range. Thereafter, there was a rapid increase of sulfur up to 2.82% in the $C_{16}$ fraction. It is noted that there was increasing decomposition during the distillation of these fractions. When the $C_{16}$ fraction was redistilled a broad molecular weight range of 1-n-olefins was found in the distillates.

TABLE IV

Elemental Composition of Light Fluid Coker Gas Oil

| Gas Oil Carbon Number | | $C_9$ | $C_{10}$ | $C_{11}$ | $C_{12}$ | | | | $C_{13}$ | $C_{14}$ | $C_{15}$ | $C_{16}$ |
|---|---|---|---|---|---|---|---|---|---|---|---|---|
| Boiling Point, °F. | Initial | 293 | 335 | 365 | 405 | 405 | 412 | 415 | 423 | 442 | 475 | 505 | 525 |
| (Calcd. for 1 Atm) | Final | 307 | 345 | 385 | 425 | 412 | 415 | 423 | 425 | 454 | 485 | 522 | 535 |
| Carbon, % | | 86.10 | 85.62 | 85.77 | 86.17 | 85.71 | 85.11 | 85.48 | 86.14 | 85.74 | 85.65 | 84.51 | 84.77 |
| Hydrogen, % | | 12.58 | 12.40 | 12.81 | 12.29 | 11.79 | 12.47 | 12.47 | 12.89 | 11.92 | 11.69 | 11.69 | 12.22 |
| Total Sulfur, % | | 1.06 | 1.06 | 1.01 | 1.15 | 1.39 | 1.14 | 0.96 | 0.97 | 1.56 | 2.34 | 2.62 | 2.82 |
| Total Nitrogen, % | | .0163 | .0244 | .0243 | 0.131 | .0294 | .0364 | .0352 | .0289 | .0395 | .0306 | .0652 | .0713 |
| Mercaptan Sulfur, % | | .0084 | | 0.105 | .0118 | .0132 | .0115 | .0116 | .0127 | .0061 | .0084 | .0825 | 0.1395 |
| Sulfur Compounds, %[a] | | 4.17 | 4.63 | 4.86 | 5.53 | 6.69 | 5.49 | 4.62 | 4.68 | 7.50 | 12.28 | 14.90 | 17.27 |

The weight percentages of sulfur compounds were calculated on the basis of total sulfur found assuming that the sulfur compounds were $C_3$ to $C_5$ alkylthiophenes in the $C_9$ to $C_{11}$ olefin range, benzothiophene in the $C_{12}$–$C_{13}$ range, $C_1$ to $C_{13}$ benzothiophenes in the $C_{14}$ to $C_{16}$ range This suggests the breakdown of nonvolatile aliphatic sulfur compounds to generate olefins and mercaptans.

The total nitrogen contents of the distillates were more than an order less than that of the total sulfur. The mercaptan content is generally even lower. However, both the nitrogen and mercaptan contents rose sharply in the $C_{15}$ and $C_{16}$ fractions.

Separation of Olefinic Feed Components

It was found that fractions rich in paraffins and/or olefins and aromatic fractions can be separated from thermally cracked distillates derived from petroleum residua. On cooling such distillates of high 1-n-olefin and n-paraffin content, it was discovered that these major components cocrystallize and can thus be separated. The resulting α-olefin/paraffin mixtures can be either used as such in olefin reactions or further separated.

In a study of model compounds we established that suitable mixtures for the present separation are those which contain 1-n-olefins and paraffins having a range of carbon atoms. If the 1-n-olefin and n-paraffin components are in a single carbon fraction, they do not tend to cocrystallize or to form any solid solution. Effective cocrystallization of a n-paraffin of a certain carbon numbers occurs with a 1-n-olefin having two more carbons per molecule. Thus we found that eicosane ($C_{20}°$) cocrystallized with docosene ($C_{22}=$) while eicosane and eicosene did not.

Experiments with a $C_9-C_{19}$ fraction of Fluid-coker gas oil demonstrated that the 1-n-olefin and n-paraffin components can be separated by crystallization. This is indicated by FIG. 5 which shows the capillary gas chromatograms of this feed and the separated mixture. In the experiment illustrated by this figure, a 5% methyl ethyl ketone (MEK) solution of the feed was cooled by dry ice and filtered and washed with cold MEK to separate the 1-n-olefin - n-paraffin ($C_n= +C_n°$) mixture. A toluene solution of the separated crystals was then analyzed by capillary GC.

FIG. 5 shows that the $C_n= +C_n°$ components represent about 41.3% of the feed while 93.4% of $C_n= +C_n°$ is present in the crystalline mixture which was separated.

This method of separation could be realized with other, possibly more advantageous solvents. Olefin-paraffin mixtures could be obtained which then could be easily processed further to separate the olefins from the paraffins via molecular sieve (Parex process).

It was also found that Flexicoker and Fluid-coker distillates can 8e selectively extracted by polar solvents as sulfonates and acetonitrile to yield extracts highly enriched in aromatics including sulfur compounds. The remaining raffinate rich in paraffins and olefins is a much improved feed of greatly reduced sulfur content. n-Paraffin and n-olefin rich feeds can be similarly separated by adsorption e.g. by using zeolites. This finding is illustrated by the following tabulation showing the results of single stage extraction with sulfolane at 20° C.

| Components | Composition by GC | | |
|---|---|---|---|
| | Feed | Raffinate ~90% | Extract ~10% |
| Paraffins | 26 | 29 | 6 |
| Olefins | 64 | 66 | 49 |
| Aromatics | 10 | 5 | 39 |

The olefin rich fractions resulting from these separations and others such as adsorption can be used for the alkylation of phenol, olefins, aromatic hydrocarbons and the like. The aromatic components can be reacted with coker distillate olefins of choice of further purified and then utilized.

The present invention is further described in the following illustrative examples which, however, are not presented for the purpose of limiting the scope of the invention, but for the purposes of illustrating several embodiments thereof.

EXAMPLE 1

This example illustrates the alkylation of excess phenol with a $C_{12}$ olefin containing a fraction of Fluid-coker gas oil from a thermal cracking process.

A stirred mixture of 1035.2 g (11 mole, 100% excess) phenol and 1851.5 g of a $C_{12}$ distillate fraction of a fluid coker gas oil containing about 50% isomeric dodecenes (928 g, 5.5 moles) in a 5 liter flask was heated by a heating bath under nitrogen to 110° C. At that temperature, 419.9 g of a dry crosslinked polystyrene sulfonic acid sold under the tradename Amberlyst 15 by the Rohm and Haas Co. (equivalent to 1.97 mole sulfonic acid) was added. An immediate exothermic reaction occurred which raised the temperature of the mixture to 130° C. within 2 minutes. At that point the mixture was cooled to about 115° C. and kept at that temperature for 4 hours. Periodic analyses of the mixture by packed column chromatography indicated the following percentages of monododecylphenol and didodecylphenol:

| Reaction Time Hrs. | Dodecylphenol Products, % | |
|---|---|---|
| | Mono- | Di- |
| 1 | 35.6 | 7.1 |
| 2 | 39.6 | 7.7 |
| 4 | 44.4 | 7.8 |

These data indicate that most of the reaction took place within the first hour. Due to the excess phenol employed, the ratio of mono-vs. didodecylphenol products did not increase significantly with increasing dodecene conversion. At the end of the four hour reaction period these two products together were present in 52.2% concentration. The final weight ratios of the mono- vs. didodecylphenol were 85 to 15. On the basis of the GC data 1282 g of monododecylphenol was formed which is 88% of the calculated yield.

The final reaction mixture was filtered with suction using a glass filter of medium frit to remove the catalyst. The catalyst was then washed with toluene and the filtrates were combined and fractionally distilled in vacuo to separate the products and unreacted feed components. The monododecylphenol product was obtained at between 122° and 145° C. at 0.05 mm. The didodecylphenol was distilled between 192° C. and 200° C. at 0.05 mm. Elemental analysis was obtained. For monododecylphenol, $C_{18}H_{30}O$: Calcd. C, 82.38%; H, 11.52% found C, 82.69%; H, 10.64%; S, 0.25%. For didodecylphenol, $C_{30}H_{54}O$: Calcd. C, 83.65%; H, 12.64%. Found C, 83.90%; H, 10.39%.

The structures of the mono- and di-dodecylphenol products were also subjected to a $^{13}C$ NMR study. The monododecylphenol was determined to have 36.5% of the ortho-substituted isomer and 63.5% of the parasubstituted phenol. In the case of dodecylphenol obtained by the reaction of isododecene with phenol, the ortho isomer is much less generally in the range of 4% to 10%. The branchiness of the present semilinear monododecylphenol product was also compared with that of the highly branched isododecylphenol on the basis of the number of methyl groups present per phenyl group. That number of methyl groups is two for a linear 1-n-dodecene derivative. Monobranched dodecenes lead to products having three methyl groups. Dibranched olefins provide products having four methyl groups. The degree of branchiness of these three products is defined as 0, 1 and 2. The NMR study of the present semilinear monododecylphenol showed 2.9 mole methyl groups per molecule and thus a branchiness degree of 0.9. In contrast, the commercial isododecylphenol had 4.9 methyls and thus a branchiness of 2.9. Due to the NMR uncertainty of $CH_2$ versus $CH_3$ group assignments these values may not be absolutely right but certainly indicate the much reduced branchiness of the novel product.

The results of the comparative NMR studies of semilinear and highly branched alkylphenols are shown by Table V. The data indicate major differences between the semilinear and branched isomers of dodecylphenols and nonylphenols both with regard to the percentages of ortho - ortho isomers and the methyl branching number.

The above comparative data on the ortho to para isomer ratios and the degrees of branchiness of the semilinear and branched nonylphenols are qualitatively displayed by their $^{13}C$ NMR spectra in FIG. 6. In the aromatic carbon region of 100 to 160 ppm, the figure shows that the semilinear product has more o-substituted carbons (C—C o in the 132 to 136 ppm range) than the highly branched. The less branched character of the semilinear product is indicated by the aliphatic region of the spectra, between 0 to 60 ppm. It is particularly apparent that the semilinear product has fewer methyl groups in the 5 to 20 ppm region.

reaction mixture was followed by periodic chromatographic analysis and is shown by the following tabulation.

| Reaction Time Hrs. | Nonylphenol Products, % | |
|---|---|---|
| | Mono- | Di- |
| 1 | 24.8 | 2.3 |
| 2 | 29.2 | 2.7 |
| 4 | 36.3 | 6.3 |

The final reaction mixture was filtered using a Buchner funnel with suction. The Amberlyst 15 was washed twice with 400 ml n-hexane each and dried in vacuo. The resulting recovered catalyst weighted 462 g and thus showed a 19% weight increase.

TABLE VI

| | | Hydrogen and Compound Type Distribution in the Feed and Recovered Components of $C_{12}$ Billings Fluid Coker Light Gas Oil | | | | | | | |
|---|---|---|---|---|---|---|---|---|---|
| | | Types of Monoolefins (Dodecenes) | | | | | Aromatics | | |
| Sample Type | Dimension of Data | I —CH=CH$_2$ | II —CH=CH— | III —C—CH$_2$ | IV —C=CH— | Conj. Dienes | Mono- Nuclear | Naphtha lene | Par- affinic[a] |
| Feed | % H | 3.18 | 0.99 | 0.73 | 0.40 | 1.09 | 4.56 | 0.77 | 88.48 |
| Unreacted[b] | % H | 0 | 0.24 | 0 | 0 | 0 | 29.50[c] | 1.19 | 70.27 |
| Feed | % Wt | 24.0 | 11.2 | 8.3 | 9.1 | 8.1 | 21.7 | 1.7 | 16.0 |
| Unreacted | % Wt | 0 | 0.7 | 0 | 0 | 0 | — | — | — |

[a]Hydrogens on saturated carbons. Value includes alkyl hydrogens.
[b]The recovered unreacted feed contained 34% unreacted phenol.
[c]Includes phenol.

The composition of the starting $C_{12}$ light Fluid-coker gas oil fraction and the unreacted components of the same were compared by $^1H$ NMR spectroscopy. Percentages of different types of hydrogens were determined. Based on the hydrogen distribution weight percentages of the various types of compounds were estimated as shown by Table VI.

The data show that out of the roughly 60% total olefins and conjugated diolefins, about 59.3 reacted. Only about 0.7% of Type II, i.e. linear internal, dodecenes were present in the recovered feed.

TABLE V

Comparison of Semilinear and Highly Branched Alkylphenols by $^{13}$ NMR Spectroscopy

| Type of Alkylphenol | Carbon % | | | Ortho Isomer % | Methyl Branching No. |
|---|---|---|---|---|---|
| | Aromatic | Aliphatic | Methyl[a] | | |
| Semilinear Dodecyl | 37.7 | 62.3 | 18.1 | 36.5 | 0.9 |
| Branched Dodecyl | 33.2 | 66.8 | 26.8 | 5.9 | 2.9 |
| Semilinear Nonyl | 42.2 | 57.8 | 16.4 | 19.3 | 0.3 |
| Branched Nonyl | 39.5 | 60.5 | 27.8 | 5.0 | 2.2 |

[a]Methyl carbons are estimated based on the mole fraction of saturated carbon peaks between 26 and 5 ppm, excluding the 22.5 ppm methylene peak. The methyl carbons of t-butyl and neopentyl groups are not included.

EXAMPLES 2 AND 3

This example, illustrates the alkylation of phenol with excess C$_9$ olefin containing a fraction of Fluid-coker gas oil.

A stirred mixture of 591 g (6.28 moles) phenol and 2000 g of a C$_9$ fraction in a fluid coker gas oil containing about 60% nonenes (1200 g, 9.51 moles) in a 5 liter flask was heated by a heating bath to 110° C. At that temperature, 388.7 g of a sulfonic acid catalyst was added. A mild exotherm occured. The reaction mixture was kept at 115° C. for 4 hours. The product formation in the The recovered catalyst was used in Example 3 which was carried out in the same manner. The results were also similar:

| Reaction Time Hrs. | Nonylphenol Products, % | |
|---|---|---|
| | Mono- | Di- |
| 1 | 21.6 | 1.8 |
| 2 | 28.0 | 4.0 |
| 4 | 34.9 | 3.4 |

The resulting reaction mixture was filtered and the catalyst was washed in the same manner, except that toluene was used for washing. The use of toluene resulted in the recovery of a cleaner catalyst. The dried weight of the catalyst was 411 g, just 6% above the original.

The average percentage of mononoylphenol in the above examples was 35.6%. The average ratio of mono- versus dinonylphenol was 85 to 15. On the basis of the GC data the weight of the combined product is 1845 g. This corresponds to 66.7% of the calculated yield.

The combined filtrates and washings were fractionally distilled in vacuo to separate the uncoverted reactants and products. The unconverted $C_{12}$ fraction was distilled at first about 40° C. at 1 mm. It was a colorless liquid. This was followed by the unconverted phenol at about 60° C. at 0.1 m. The product was distilled with minor decomposition, essentially dealkylation, apparently due to the presence of residual acid catalyst. Thus some of the crude product distillates were combined and redistilled to provide a total of 1489 g (53.8%) of mononoylphenol as an almost colorless liquid boiling in the range of 105° and 120° at 0.05 mm. The dinonylphenol by-product boiled between about 160° and 182° C. at 0.05 mm. The amount of this viscous orange liquid distillate product was 204 g.

Analysis was as follows: Mononoylphenol, $C_{15}H_{24}O$. Calcd. C, 81.76%; H, 10.98%. Found C, 82.90%; H, determined by GC. The data obtained are shown in the following.

TABLE VII

Hydrogen and Compound Type Distribution in the Feed and Recovered Components of $C_9$ Billings Coker Naphtha

| Sample Type | Dimension of Data | Types of Monoolefins (Nonenes) | | | | Total Mono-Olefins | Conj. Dienes | Arom-atics[c] | Par-affinic[a] |
|---|---|---|---|---|---|---|---|---|---|
| | | I —CH=CH$_2$ | II —CH=CH— | III —C=CH$_2$ | IV —C=CH— | | | | |
| Feed | % H | 4.35 | 1.12 | 0.90 | 0.58 0.61 | 8.33 | 1.39 | 4.37 | 87.30[a] |
| Unreacted[b] Feed | % H | 0.34 | 2.13 | 0 | | 3.07 | 0 | 16.58 | 77.73[a] |
| | Wt % | 25.2 | 9.8 | 7.8 | 10.1 9.4 | 52.9 | 7.9 43.8 | 14.2 | 24.9 |
| Unreacted[b] | Wt % | 1.7 | 16.4 | 0 | | 27.5 | 0 | | 27.7 |

[a]Hydrogens on saturated carbons. Value includes alkyl hydrogens.
[b]The recovered unreacted feed contained 34 wt % toluene.
[c]Includes toluene solvent.

10.59%; S, 0.15%. Dinonylphenol, $C_{24}H_{42}O$. Calcd. C, 83.17%; H, 12.22%. Found: C, 83.41%; H, 10.38%; S, 0.58%.

A study of the distilled mononoylphenol fraction by $^{13}C$ NMR spectroscopy indicated that the nonyl groups were more branched than the dodecyl groups of the product of Example 1. The increased branchiness of the alkyl groups in the present case is apparently the result of low olefin conversion. (At low olefin conversion, only the more branched olefin components of the cracked distillate react under selective alkylation conditions). NMR also showed that the ratio of ortho-nonylphenol to para-nonylphenol was 19 to 81. This ortho/para ratio is less than half of that observed in the case of ortho and para-dodecylphenols. Again, the lower ortho/para ratio is due to the increased branching of the alkyl substituents.

The composition of the starting $C_9$ Fluid-coker naphtha fraction and the recovered unreacted components of the same were compared by $^1H$ NMR spectroscopy. The results are shown by Table VII. The data of the table indicate that the mono-olefin components, i.e., nonenes, were only partially converted to nonylphenols. Much of the Type I olefin, 1-n-nonene, was isomerized to Type II olefins, internal olefins. However, only part of the latter reacted further to yield the desired alkylphenol products.

Although the nonylphenol of the present example is of a more branched character than the analogous product of Example 1, it is nevertheless distinctly different from the highly branched t-nonylphenols of the prior art. This has been determined by comparison of the $^{13}C$ NMR spectra of the product of this experiment and t-nonylphenol.

EXAMPLE 4

This example demonstrates the alkylation of phenol with a $C_8$ fraction of a fluid coker naphtha containing equimolar amounts of octenes.

A magnetically stirred mixture of 1.2 g (12.75 mmole of phenol and 2.4 g of a $C_8$ distillate cut of a Fluid-coker naphtha containing 60% (1.43 g, 12.75 mmole) of octenes and 0.54 g of catalyst that was used in the type of Example 1 was heated in a closed vial at 90° C. for 8 hours. In a second run, an identical reaction mixture was employed; however, the temperature used was 115° C. In a third run, a $C_8$ coker naphtha was replaced by a 60/40 weight mixture of 1-octene and n-nonane. This mixture was then reacted with phenol in the same manner at 115° C. to obtain the comparative data on its reactivity. The percentages of mono- and dioctyphenols formed in the three reaction mixtures were periodically determined by GC. The data obtained are shown in the following.

| Reaction Time Hours | Mono- and Dioctylphenol Products, % | | | | | |
|---|---|---|---|---|---|---|
| | Run 1 Octenes, 90° | | Run 2 Octenes, 115° | | Run 3 1-Octene, 115° | |
| | Mono- | Di- | Mono- | Di- | Mono- | Di- |
| 1 | 13.8 | 0.4 | 33.7 | 2.9 | 28.59 | 2.3 |
| 2 | 18.7 | 1.2 | 42.2 | 5.1 | 33.74 | 4.9 |
| 4 | 25.3 | 1.5 | 36.37 | 16.2 | | |
| 8 | 32.8 | 2.3 | | | | |

The results show that the alkylation of phenol in the presence of Amberlyst 15 is much faster at 110° C. than at 90° C. At 115° C., the reaction with the $C_8$ cut of coker naphtha is essentially complete in 2 hours. At comparable dilution, 1-n-octene is less reactive but eventually leads to more dialkylated phenol than the isomeric octenes of coker naphtha.

EXAMPLE 5

This example demonstrates the alkylation of phenol 130° C. with a $C_9$ Fluid-coker naphtha containing a small excess of olefins.

Phenol was reacted with 10% excess of Fluid-coker nonenes at 130° C. in the presence of 5 wt. % Amberlyst 15 in the manner described in Examples 2 and 3. The data indicate that the conversion was substantially complete in 4 hours. The ratio of mono-versus dinonylphenol products was found to be substantially similar to those of Examples 2 and 3 in spite of the different ratios of reactants used.

The final reaction mixture was worked up to obtain mono- and dinonylphenol products via fractional distillation. The first distillate fractions containing the more branched nonylphenol isomers was obtained between 94° and 104° C. at 0.05 mm. The latter distillate fractions with the more linear nonylphenols were distilled between 104° and 119° C. at 0.5 mm. Both sets of distillates were of similar amounts and found to be similar in composition, thus confirming their isomeric character.

Elemental Analyses. Mononoylphenol, $C_{15}H_{24}O$. Calcd: C, 81.76; H, 10.98. Found for first distillate: C, 82.04; H, 10.10; S, 0.25. Found for second distillate, C, 82.50; H, 9.84; S, 0.15. Dinonylphenol, $C_{24}H_{42}O$. Calcd: C, 83.17; H, 12,22. Found: C, 83.41; H, 10.01; S, 0.35.

EXAMPLE 6

This example demonstrates the alkylation of phenol with equimolar $C_9$ olefin containing fraction of Fluid-coker naphtha, at 150° C.

A magnetically stirred mixture of 1.8 g (19 mmole) phenol, 4 g of a C$_9$ distillate cut of Fluid-coker naphtha, containing 60%, i.e.. 2.4 g (19 mmole) of nonenes, and 0.29 g (5 wt. %) Amberlyst (1.4 mmole sulfonic acid equivalent) was heated at 85° C. for 16 hours and then at 150° C. for 8 ½ hours. During the reaction, samples of the liquid reaction mixture were periodically taken and analyzed for mono- and dinonyl phenol. The data obtained are shown in the following.

| Reaction Conditions | | Nonylphenols % | |
|---|---|---|---|
| Temperature °C. | Time Period Hours | Mono- | Di- |
| 85 | 16 | 14.4 | |
| 150 | +2 | 38.3 | 4.0 |
| | 4 | 42.5 | 4.5 |
| | 8 | 45.0 | 6.0 |

The results show that at 85° C. little reaction occurs while at 150° C. mono-octylphenol is formed rapidly and selectively.

EXAMPLES 7 TO 9

This example shows the effect of varying temperatures and reactant ratios on the alkylation of phenol with an olefinic C$_9$ fraction of Fluid-coker naphtha.

Magnetically stirred mixtures of phenol and a C$_9$ distillate cut of Billings Fluid Coker naphtha of 60% nonenes content were reacted in the presence of 15% Amberlyst catalyst in the manner described in Example 6. Different reaction temperatures and phenol to nonenes reactant ratios were used. The mixtures were periodically samples and analyzed by GC. The data obtained are shown by Table VIII.

Comparison of the data of Examples 6 and 7 indicates that the reaction is considerably faster at 130° than at 115° C. However, the reaction rate could be sufficiently increased at 115° C. by increasing the amount of catalyst used. Thus the rate at 115° C. in the presence of 15% Amberlyst in Example 8 was found to be similar to that obtained at 130° C. in the presence of 5% Amberlyst in Example 4.

TABLE VIII

Effect of Reactant Ratios on Phenol Alkylation with C$_9$ Fluid-coker Naphtha

| Example No. | Phenol to Nonenes Ratio | Reaction Conditions | | Nonylphenols in Mixture % | |
|---|---|---|---|---|---|
| | | Temperature °C. | Time Period Hours | Mono- | Di- |
| 7 | 0.90 | 130 | 1 | 38.3 | 6.3 |
| | | | 2 | 49.4 | 9.5 |
| | | | 4 | 48.3 | 12.1 |
| | | | 8 | 51.9 | 20.3 |
| 8 | 0.90 | 115 | 1 | 22.0 | 4.7 |
| | | | 2 | 30.3 | 4.8 |
| | | | 4 | 36.8 | 6.3 |
| | | | 8 | 40.2 | 8.3 |
| 9 | 0.66 | 115 | 1 | 19.8 | 2.9 |
| | | | 2 | 29.2 | 5.6 |
| | | | 4 | 30 | 9.2 |
| 9 | 0.50 | 115 | 1 | 12.5 | 2.7 |
| | | | 4 | 25.7 | 8.6 |

A decreasing phenol to olefin ratio from 0.9 to 0.5 in Examples 7 to 9 resulted in decreased product formation. It is apparently advantageous to employ phenol in excess of the amount reacted to increase the reaction rate and selectivity.

EXAMPLE 10

This example shows a model compound study of phenol alkylation with 1-octene in the presence of benzothiophene.

In a magnetically stirred, closed vial, a mixture of equimolar amounts of phenol and benzothiophene [0.94 g, (10 mmole) phenol and 1.34 g (10 mmole) benzothiophene] and an equivalent amount of 1-octene (1.12 g, 10 mmole) was reacted in the presence of 0.17 g Amberlyst 15 (5 wt %) at 80° C. overnight. GC analyses of the reaction mixture by packed column and capillary GC indicated that the octene selectively alkylated the phenol. According to packed column GC, the reaction mixture contained 16% monooctylphenols and 1% monooctylbenzothiophenes. No significant amounts of either dioctylphenols or dioctylbenzothiophenes were formed. Capillary GC indicated an extensive isomerization of the starting 1-octene reactant. Only 11.2% of the total octenes in the reaction mixture was 1-octene. o-Octyl-phenols and p-octylphenols constituted about 83% of the octylphenols. The remaining 17% were assumed to be m-octylphenols. In the case of both o-octylphenols and p-octylphenols the 2-methylheptyl-phenols were the main isomers. They were about 70% of the total. On further heating of the mixture dioctylphenols were formed, mostly via the further alkylation of o-octylphenols. Thus the resulting mixture consisted mostly of p-octylphenols and o, p-dioctylphenols; o-octylphenols were absent.

The results of phenol alkylation by 1-octene alone at 115° C. were qualitatively similar. The most apparent difference was the increased isomerization of 1-octene and reduced percentages, about 55%, of the 2-methylheptylphenol isomers compared to the other isooctylphenols. Overall, the study confirms the selective course of phenol alkylation by Fluid coker olefins.

Procedure for the Alkoxylation of Semilinear Alkylphenols (EXAMPLES 11 TO 15)

The ethoxylation and propoxylation of alkylphenols, derived from Fluid coker distillates in previous examples, were mostly carried out in pressure tubes of about 9 ml capacity. These tubes were equipped with a Teflon screw valve and fit for use in a JEOL FX90Q multinuclear NMR spectrometer. Usually about 3 g of a reaction mixture was employed.

In a typical procedure, the alkylphenol and the catalyst and a nonvolatile solvent, typically mesitylene, were added to the pressure tube. If sodium was used as a catalyst precursor, it was dissolved in the alkylphenol to form sodium alkphenolate prior to being added into the tube. The last component to be added was ethylene oxide or propylene oxide. Appropriate molar amounts of ethylene oxide were condensed to the other components into the evacuated tube which was then closed. The liquid propylene oxide reactant was simply added to the mixture. The closed tubes containing the reaction mixtures were then heated in baths at the desired reaction temperature. At the start of the heating the mixture was shaken by hand to assure homogeneity. During the reaction, samples were periodically taken from the tubes, after cooling, for GC analyses to determine the progress of the reaction.

In most of the alkoxylations, a monononylphenol product of Example 5 was used as a starting reactant.

This reactant was an early distillate fraction and as such contained 0.25% sulfur in the form of alkylthiophenes. The latter, of course, do not react with epoxides. However, they tend to polymerize in the presence of strong acids.

EXAMPLE 11

This example illustrates the ethoxylation of semilinear nonylphenol.

Into each of four pressure tubes was placed 2.2 g (10 mmole) nonylphenol prepared in accordance with the process of this invention and 2.2 g mesitylene solvent. Five percent of the nonylphenol was present as sodium nonylphenolate derived by the reaction of 0.012 g (0.5 mmole) sodium with the phenol. Thereafter, varying amounts of ethylene oxide were condensed into the tubes; 15, 20, 30 and 100 mmoles, respectively. This resulted in ethylene oxide to nonylphenol reactant ratios of 1.3, 2, 3 and 10.

The tubes were sealed and heated at 140° C. The first three mixtures were kept at that temperature for 1 hour, the last for 15 minutes. Thereafter they were analyzed by packed column GC. The GC data indicated a complete reaction of ethylene oxide with the exception of the 15 minute sample. The nonylphenol reactant was substantially converted in each case. However, the impurities in the nonylphenol, apparently nonylthiophenes of shorter retention times, did not react.

GC indicated the formation of ethoxylated nonylphenol products. The ratios of the variously ethoxylated nonylphenols were different, clearly dependent on the ethylene oxide to nonylphenol reactant ratios. The results are shown by Table IX.

TABLE IX

| Effect of Reactant Ratios on the Degree of Ethoxylation of Semilinear Nonylphenol | | | | |
|---|---|---|---|---|
| No. of Ethoxy Units Per Mole Product | Distribution of Various Ethoxylated Products, GC% (At Varying Ethylene Oxide Nonylphenol Ratio) | | | |
| | (1.3) | (2) | (3) | (10) |
| 1 | 50.3 | 18.1 | 7.2 | 11.2 |
| 2 | 49.7[b] | 76.1 | 38.5 | 16.2 |
| 3 |  | 5.8[b] | 54.3[b] | 32.4 |
| 4 |  |  |  | 40.2[b] |

[a]The mixture of 10/1 ethylene oxide to nonylphenol was reacted for only 15 minutes.
[b]This percentage includes the species of higher ethoxylation as well.

Due to the complexity of the Fluid-coker nonenes feed, a high number of isomeric compounds was formed. Thus the distinction between compounds of varying ethoxylation degrees was difficult and somewhat arbitrary. However, comparatively valid distribution data were obtained since the same assumptions were made in evaluating all the reaction mixtures.

At the low ethylene oxide to nonylphenol ratio of 1.3, only mono-and diethoxylated products were formed. At the oxide to phenol ratio of 3 most of the products had 2 or 3 ethoxy units per molecule. In contrast, at an oxide to phenol ratio of 10 a broad distribution of ethoxylated products was obtained. The degree of ethoxylation extended far beyond four, even though not all the ethylene oxide reacted in the short, 15 minutes, reaction time.

EXAMPLE 12

This example illustrates the propoxylation of semilinear nonylphenol.

The nonylphenols derived in accordance with the present invention reacted with varying amounts of propylene oxide in a manner analogous to Example 11 above. These reactions were carried out in the presence of 5 mole % sodium as catalyst precursor. Propylene oxide to nonylphenol reactant ratios of 1, 2 and 10 were used. The reaction mixtures were heated at 140° C. and periodically sampled for GC analyses. At the 1/1 and 3/1 oxide to phenol reactant ratios, selective propylene oxide ring opening by the phenol took place. On the basis of GC composition, the relative amounts of variously propoxylated nonylphenols were calculated. The data are shown in Table X.

TABLE X

| Effect of Reactant Ratios on the Degree of Propoxylation of Semilinear Nonylphenol | | | | | |
|---|---|---|---|---|---|
| No. of Propoxy Units Per Mole | Distribution of Various Propoxylated Products % by GC | | | | |
| | Oxide to Phenol Ratio 1 | | | Oxide/Phenol = 3 | |
| | 30 Min.[a] | 1 Hr.[a] | 3 Hrs. | 1 Hr.[a] | 2 Hrs. |
| 1 | 89.2 | 83.8 | 58.6 | 11.7 | 5.0 |
| 2 | 10.8 | 16.2 | 41.4[b] | 39.7 | 39.5 |
| 3 |  |  |  | 27.1 | 36.2 |
| 4 |  |  |  | 21.5[b] | 19.3[b] |

[a]The reaction mixture contained unreacted propylene oxide.
[b]Includes species of higher propoxylation.

The data indicate that as the reaction progressed, the amounts of more highly propoxylated species increased. At a nominally equimolar reactant ratio (due to impurities in the phenol the real ratio was greater than one) the main products were mono- and dipropoxylate. When a threefold excess of propylene oxide was used, the main products were di- and tripropoxylated nonylphenols. Beyond the tetrapropoxylated species, little product was formed.

In contrast to the above selective reactions at low propylene oxide to phenol ratio, propylene oxide polymerization became a major side reaction when 10 moles of oxide were reacted with one mole of phenol at 140° C.

EXAMPLE 13

This example compares the base and acid catalyzed ring opening reactions of propylene oxide with monoethoxylated phenol as a model compound.

Monoethoxylated phenol was reacted with propylene oxide in the presence of sodium as a catalyst precursor and 15 wt. % p-toluene sulfonic acid as a catalyst. The sodium was reacted with the monoethoxylated phenol to provide 5 mole % sodium alcoholate as a catalyst. In both experiments, 2.76 g (10 mmole) monoethoxylated phenol, 2.76 g mesitylene solvent and 1.16 g (10 mmole) propylene oxide were employed. The reactions were carried out in closed pressure tubes as usual at 140° C. for 1 hour.

In the presence of the base catalyst, propylene oxide conversion was complete and a highly selective ring opening reaction took place to form compounds of the generic formula.

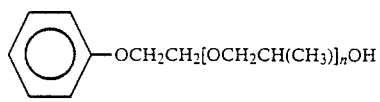

GC analyses indicated the following percentage distribution for the variously propoxylated secondary alcohol products: n=0: 9.6; n=1: 64.9; n=3: 18.2; n=4: 4.5; n=5: 2.8.

The acid catalyst was not soluble in the reaction mixture at room temperature but dissolved on heating. Acid catalysis was somewhat less effective and less selective than base catalysis. After one hour at 140° C., there was still 1% unconverted propylene oxide (6.5% of the original amount) in the reaction mixture. Also, there was 5.77% propylene oxide oligomer present (equivalent to 37% of the propylene oxide reactant employed) and 26.8% of monoethoxylated phenol. The major part of the propylene oxide (57.2%) reacted with the monoethoxylated phenol to form primary and secondary alcohols. The ratio of these alcohols for the monopropoxylated products according to capillary GC was the following:

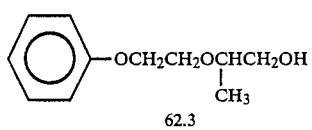
62.3

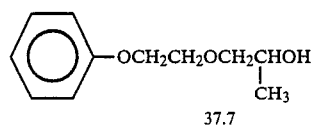
37.7

These two compounds represent 75% of the propoxylated products. The other 25% consists mostly of isomeric dipropoxylated products.

EXAMPLES 14 AND 15

These examples describe the propoxylation of ethoxylated nonylphenols of this invention in the presence of base and acid catalysts.

As a reactant in these examples, an ethoxylated semilinear nonylphenol was used. It contained almost equal quantities of the mono-and diethoxylated nonylphenols in mesitylene solution. (As a catalyst 5 mole % the sodium alcoholate derivative was present.) The results were analogous to those observed with the model compounds in the previous examples.

In the first example, 2.15 g of the above reactant was reacted with a threefold excess (0.75 g) of propylene oxide in a pressure tube. On heating the reaction mixture at 140° C. for 1 hour, a base catalyzed reaction took place. GC analysis indicated that the ethoxylated reactants were essentially all propoxylated. Most of the propylene oxide employed (90%) was reacted selectively without any propylene oxide oligomer formation.

A comparative experiment (Example 15) was carried out in an identical manner, except for the acid catalyst. To the ethoxylated nonylphenol reactant (2.15 g), 0.37 g p-toluenesulfonic acid monohydrate was added to neutralize the sodium alkoxide base and provide a 15% concentration of the acid catalyst. Thereafter, a threefold molar excess of the propylene oxide reactant (0.75 g) was added and the sealed mixture was heated at 140° C. for 1 hour. A subsequent GC analysis indicated that propoxylation occured but at a lower rate and less selectively than in the case of the base catalyst.

EXAMPLE 16

This example illustrates the reaction of nonylphenol sodium compound prepared in accordance with the present invention and n-octylphenol sodium with γ-butanesultone.

For the first run, 2.2 g of a nonylphenol prepared in accordance with this invention was reacted with 2.2 g of 25% methanolic sodium methoxide, containing 10 mmoles of base. To the resulting sodium nonylphenolate solution, 1.4 g (10 mmole) γ-butanesultone was added to provide a clear orange reaction mixture liquid. The reaction occurred on standing at room temperatures. It was indicated by the precipitation of colorless 3-nonylphenylbutanesulfonic acid sodium crystals. Precipitation occurred overnight. About 0.4 g of the crystalline product was isolated by filtration and drying. Its structure was confirmed by $C^{13}$ NMR spectroscopy.

In the second run, a similar reaction was carried out with highly pure n-octylphenol to determine the characteristic NMR parameters of its 3-butane-sulfonate. These parameters were then used as diagnostic values in the confirmation of the structure of the nonyl derivative set forth above.

A solution of n-octylphenol sodium was prepared using 0.67 g (3.2 mmole) n-octylphenol, 0.14 g (3.5 mmole) sodium hydroxide and about 3 g of a 4/1 water/dioxane mixture with $D_2O$ locking solvent. To this reactant solution 0.44 g (3.2 mmole) γ-butane-sultone was added and sulfonate formation was followed by $^{13}C$ NMR. NMR showed that the sulfonate conversion was complete on standing overnight. Reaction was also indicated by the formation of product crystals. The mixture was heated at 70° C. to obtain a homogeneous solution and then a $^{13}C$ NMR spectrum was taken at that temperature. The following characteristic chemical shift values (ppm) were found for carbon fragments of the 3-butanesulfonate group.

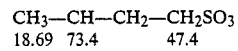

Values in the above chemical shift range were also found for the analogous sulfonate product derived from the semilinear nonylphenol.

What is claimed is:

1. A composition comprising of a mixture of alkoxylated semilinear ortho and para alkylphenols of the formula

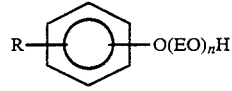

wherein R is a $C_5$ to $C_{35}$ alkyl group having an average of less than 2 branches and the ratio of ortho- to para isomers being in the range from about 10 ortho to 90 para to 40 ortho to 60 para;
E is selected from the group consisting of $CH_2CH_2$, $CH(CH_3)CH_2$ and $CH_2CH(CH_3)_n$ is 1 to 30.

2. The composition of claim 1 where R is nonyl and E is $CH_2CH_2$.

3. Monoethoxylated semilinear nonylphenol according to claim 1.

4. An alkylation process comprising reacting an olefinic cracked petroleum distillate feed produced from petroleum residua by high temperature thermal cracking and containing 1-n-olefins as the major type of olefin component and organic sulfur components in concentrations exceeding 0.1% sulfur with phenol or cresol at temperatures between 20° and 450° C. in the liquid phase in the presence of a strong acid catalyst in effective amounts to product alkylphenols as the major products, and additionally reacting the alkylphenol product with a reagent selected from the group consisting of ethylene oxide, propylene oxide, propanesultone, butanesultone, sulfur dichloride, formaldehyde, and phosphorus pentasulfide.

5. The process of claim 4 wherein the alkylphenol is reacted with ethylene oxide or propylene oxide to produce an ethoxylated or propoxylated alkylphenol nonionic surfactants.

* * * * *